US007846426B2

(12) United States Patent
Metzger et al.

(10) Patent No.: US 7,846,426 B2
(45) Date of Patent: Dec. 7, 2010

(54) COMPOSITIONS AND METHODS FOR TREATING AND PREVENTING CARDIOMYOPATHY AND HEART DISEASE

(75) Inventors: Joseph M. Metzger, Ann Arbor, MI (US); Dewayne Townsend, Ann Arbor, MI (US); Soichiro Yasuda, Ann Arbor, MI (US); Daniel E. Michele, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/885,304

(22) PCT Filed: Feb. 27, 2006

(86) PCT No.: PCT/US2006/006862

§ 371 (c)(1),
(2), (4) Date: Jun. 25, 2008

(87) PCT Pub. No.: WO2006/091941

PCT Pub. Date: Aug. 31, 2006

(65) Prior Publication Data

US 2008/0260681 A1    Oct. 23, 2008

Related U.S. Application Data

(60) Provisional application No. 60/656,570, filed on Feb. 25, 2005.

(51) Int. Cl.
*A61K 31/77* (2006.01)
(52) U.S. Cl. ..................... 424/78.38; 435/375
(58) Field of Classification Search ............... 424/78.38
See application file for complete search history.

(56) References Cited

U.S. PATENT DOCUMENTS

| 6,342,247 | B1 | 1/2002 | Ku et al. |
| 6,747,064 | B2 | 6/2004 | Emanuele |
| 6,761,824 | B2 | 7/2004 | Reeve |
| 6,977,045 | B2 | 12/2005 | Reeve |

FOREIGN PATENT DOCUMENTS

| WO | 02/065834 A | 8/2002 |
| WO | 92/22202 | 12/2002 |

OTHER PUBLICATIONS

Schaer et al (Beneficial effects of RheothRx injection in patients receiving thrombolytic therapy for acute myocardial infarction. Circulation. Aug. 1, 1996;94(3):298-307).*
Gibbs et al (Purified poloxamer 188 for sickle cell vaso-occlusive crisis. Ann Pharmacother. Feb. 2004;38(2):320-4. Epub Dec. 30, 2003).*
Yasuda et al (Membrane Sealant Poloxamer 188 Corrects the Primary Defect Caused by Dystrophin Deficiency in Single Cardiac Myocytes from Mdx Mice. Circulation, vol. 110, No. 17, Suppl. S, Oct. 2004).*
Finstere et al (The heart in human dystrophinopathies. Cardiology. 2003;99(1):1-19).*
Adams-Graves et al., "RheothRx (poloxamer 188) injection for the acute painful episode of sickle cell disease: a pilot study." 1997 Blood 90 pp. 2041-2046.
Chareonthaitawee et al., "The impact of time to thrombolytic treatment on outcome in patients with acute myocardial infarction. For the CORE investigators (Collaborative Organisation for RheothRx Evaluation)" 2000 Heart 84:142-148.
Emanuele et al., "FLOCOR: a new anti-adhesive, rheologic agent." 1998 Expert Opin Investig Drugs. 7:1193-1200.
Finsterer and Stollberger, "The heart in human dystrophinopathies." 2003 Cardiology 99 pp. 1-19.
Gibbs and Hagemann, "Purified poloxamer 188 for sickle cell vaso-occlusive crisis" 2004 Ann. Pharmacother. 38:320-324.
Goyenvalle et al., "Rescue of dystrophic muscle through U7 snRNA-mediated exon skipping." 2004 Science 306 pp. 1796-1799.
Gregorevic et al., "Systemic delivery of genes to striated muscles using adeno-associated viral vectors" 2004 Nat Med 10, pp. 828-834.
Grover et al., "Effect of a nonionic surface-active agent on blood viscosity and platelet adhesiveness" 1969 Circ. 39 and 40:I249 (Suppl. I ).
Hunt et al., "ACC/AHA Guidelines for the Evaluation and Management of Chronic Heart Failure in the Adult: Executive Summary A Report of the American College of Cardiology/American Heart Association Task Force on Practice Guidelines (Committee to Revise the 1995 Guidelines for the Evaluation and Management of Heart Failure): Developed in Collaboration With the International Society for Heart and Lung Transplantation; Endorsed by the Heart Failure Society of America." 2001 Circulation 104:2996-3007.
Kabanov et al., "Pluronic block copolymers for overcoming drug resistance in cancer" 2002 Adv Drug Deliv Rev, 54, 758-779.
Kaprielian and Severs, "Dystrophin and the cardiomyocyte membrane cytoskeleton in the healthy and failing heart." 2000 Heart Failure Reviews 5:221-238.
Kawada et al., "A novel paradigm for therapeutic basis of advanced heart failure—assessment by gene therapy" 2005 Pharmacol. Therap. 107:31-43.
Lee et al., "Pharmaceutical therapies for sealing of permeabilized cell membranes in electrical injuries." 1999 Ann NY Acad Sci 888, 266-73.
Lee et al., "Surfactant-induced sealing of electropermeabilized skeletal muscle membranes in vivo." 1992 Proc. Natl. Acad. Sci. USA 89:4524-4528.

(Continued)

*Primary Examiner*—Jake M. Vu
(74) *Attorney, Agent, or Firm*—Casimir Jones SC

(57) ABSTRACT

The present invention relates to compositions and methods for treating and preventing heart disease. In particular, the present invention provides compositions comprising poloxamers (e.g., poloxamer 188—P188) and methods of using the same for treating and preventing heart disease (e.g., in subjects with muscular dystrophy) and for treating cells and tissue damage caused by ischemia and cell death (e.g., for treating dystrophin-deficient cells (e.g., myocytes)).

12 Claims, 8 Drawing Sheets

OTHER PUBLICATIONS

Maskarinec et al., "Direct observation of poloxamer 188 insertion into lipid monolayers" 2002 Biophys. J. 82:1453-1459.

Michele et al., "Cardiac dysfunction in hypertrophic cardiomyopathy mutant tropomyosin mice is transgene-dependent, hypertrophy-independent, and improved by beta-blockade" 2002 Circ Res 91 pp. 255-262.

MODI, "Flocor CytRx Corp" 1999 IDrugs, Current Drugs Ltd, GB vol. 2 No. 4 366-374.

Muntoni, "Cardiomyopathy in muscular dystrophies" 2003 Curr. Opin. Neurol. vol. 16 pp. 577-583.

O'Keefe et al., "Poloxamer-188 as an adjunct to primary percutaneous transluminal coronary angioplasty for acute myocardial infarction" 1996 Am. J. Cardiol. 78:747-750.

Pasternak et al., "Mechanical function of dystrophin in muscle cells" 1995 J Cell Biol 128 pp. 355-361.

Raev,"Which left ventricular function is impaired earlier in the evolution of diabetic cardiomyopathy? An echocardiographic study of young type I diabetic patients" 1994 Diabetes Care 17:633-639.

Schaer et al., "Beneficial effects of RheothRx injection in patients receiving thrombolytic therapy for acute myocardial infarction: Results of a randomized, double-blind, placebo-controlled trial" 1996 Circ. (American Heart Association) 94:298-307.

Schmolka, "A Review of Block Polymer Surfactants" 1977 J. Am. Oil Chem. Soc. 54 pp. 110-116.

Shibata et al., "Study of the Effects of Nebivolol Intervention on Outcomes and Rehospitalisation in Seniors with Heart Failure (SENIORS). Rationale and design"2002 Int J. Cardiol 86:77-85.

Squire et al., "Prevention of pathology in mdx mice by expression of utrophin: analysis using an inducible transgenic expression system" 2002 Hum Mol Genet 11, 3333-44.

Straub and Campbell, "Muscular dystrophies and the dystrophin-glycoprotein complex" 1997 Curr Opin Neurol 10, 168-75.

Torrente et al., "Human circulating AC133(+) stem cells restore dystrophin expression and ameliorate function in dystrophic skeletal muscle" 2004 J Clin Invest 114,pp. 182-195.

Toth K. et al., "The effect of RheothRx injection on the hemorheological parameters in patients with acute myocardial infarction" 1997 Clinical Hemorheology and Microcirculation, Ios Press, Amsterdam vol. 17 No. 2 117-125.

Wu G. et al., "Lipid corralling and poloxamer squeeze-out in membranes" 2004 Phys Rev Lett 93 028101.

Yasuda Soichiro et al., "Dystrophic heart failure blocked by membrane sealant poloxamer" 2005 Nature vol. 436 No. 7053 1025-1029.

Yasuda So-Ichiro et al., "Membrane sealant poloxamer 188 corrects the primary defect caused by dystrophin deficiency in single cardiac myocytes from Mdx mice" 2004 Circulation vol. 110 No. 17, p. 135.

Zile and Brutsaert "New concepts in diastolic dysfunction and diastolic heart failure: Part II: causal mechanisms and treatment" 2002 Circulation 105:1503-8.

Examiner's Report, Australian Patent Application No. 2006216420 dated Feb. 27, 2009.

EP Supplementary Search Report, EP Patent Application No. 06 736 222.8 dated Sep. 29, 2008.

Baczko, et al., Pharmacological activation of plasma-membrane KATP channels reduces reoxygenation-induced Ca2 + overload in cardiac myocytes via modulation of the diastolic membrane potential, British Journal of Pharmacology, vol. 141, No. 6, pp. 1059-1067, Mar. 1, 2004.

Canadian Patent Application No. 2,599,219 Office Action dated Jul. 16, 2009.

Balghith, Mohammed, "Assessment of diastolic dysfunction after acute myocardial infarction using Doppler echocardiography," Can J Cariol vol. 18 No. 1, Jan. 2002, pp. 69-77.

EP Patent Application No. 06 736 222.8 Search Dated Jan. 27, 2010.

* cited by examiner

FIGURE 4
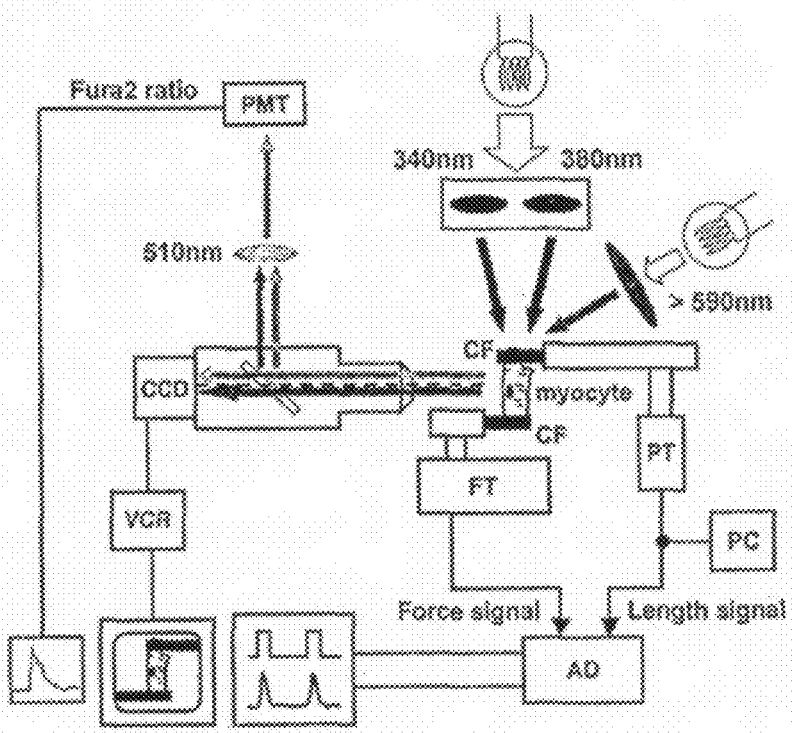
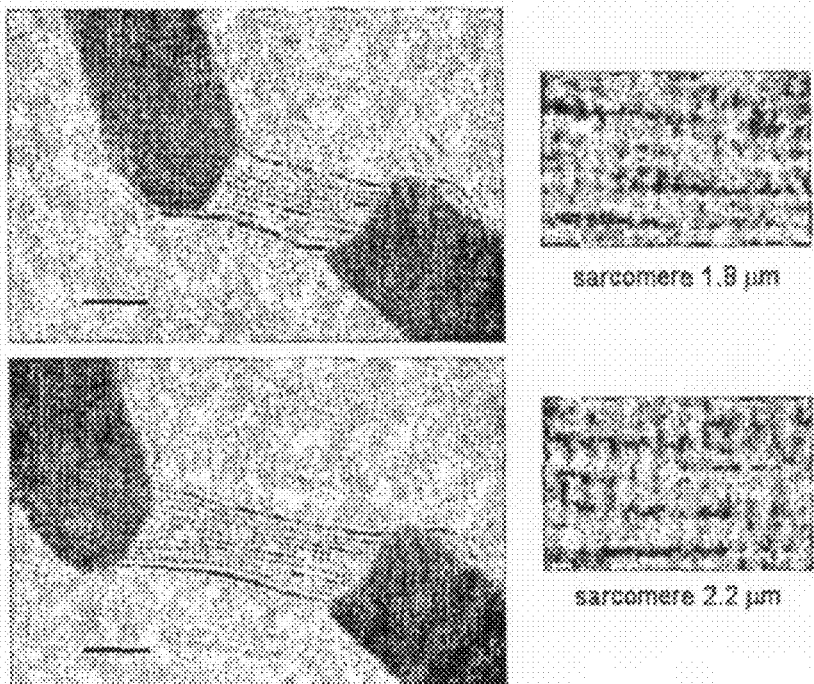
sarcomere 1.9 μm
sarcomere 2.2 μm

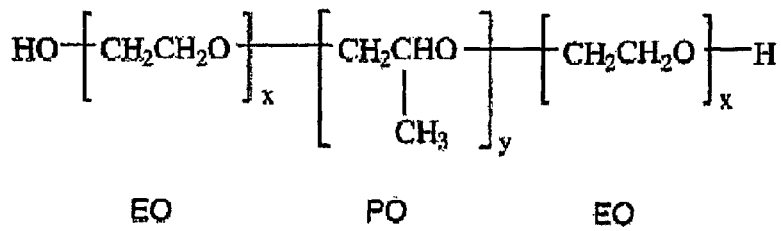

B

| Copolymer | MW[a] | Average no. of EO units $(x)$[b] | Average no. of PO units $(y)$[b] | HLB[c] | Cloud point in 1% aqueous solution (°C)[c] | CMC (M)[d] |
|---|---|---|---|---|---|---|
| L35  | 1900   | 21.59  | 16.38 | 19 | 73    | $5.3 \times 10^{-3}$ |
| L43  | 1850   | 12.61  | 22.33 | 12 | 42    | $2.2 \times 10^{-3}$ |
| L44  | 2200   | 20.00  | 22.76 | 16 | 65    | $3.6 \times 10^{-3}$ |
| L61  | 2000   | 4.55   | 31.03 | 3  | 24    | $1.1 \times 10^{-4}$ |
| L62  | 2500   | 11.36  | 34.48 | 7  | 32    | $4.0 \times 10^{-4}$ |
| L64  | 2900   | 26.36  | 30.00 | 15 | 58    | $4.8 \times 10^{-4}$ |
| F68  | 8400   | 152.73 | 28.97 | 29 | >100  | $4.8 \times 10^{-4}$ |
| L81  | 2750   | 6.25   | 42.67 | 2  | 20    | $2.3 \times 10^{-5}$ |
| P84  | 4200   | 38.18  | 43.45 | 14 | 74    | $7.1 \times 10^{-5}$ |
| P85  | 4600   | 52.27  | 39.66 | 16 | 85    | $6.5 \times 10^{-5}$ |
| F87  | 7700   | 122.50 | 39.83 | 24 | >100  | $9.1 \times 10^{-5}$ |
| F88  | 11 400 | 207.27 | 39.31 | 28 | >100  | $2.5 \times 10^{-4}$ |
| L92  | 3650   | 16.59  | 50.34 | 6  | 26    | $8.8 \times 10^{-5}$ |
| F98  | 13 000 | 236.36 | 44.83 | 28 | >100  | $7.7 \times 10^{-5}$ |
| L101 | 3800   | 8.64   | 58.97 | 1  | 15    | $2.1 \times 10^{-6}$ |
| P103 | 4950   | 33.75  | 59.74 | 9  | 86    | $6.1 \times 10^{-6}$ |
| P104 | 5900   | 53.64  | 61.03 | 13 | 81    | $3.4 \times 10^{-6}$ |
| P105 | 6500   | 73.86  | 56.03 | 15 | 91    | $6.2 \times 10^{-6}$ |
| F108 | 14 600 | 265.45 | 50.34 | 27 | >100  | $2.2 \times 10^{-5}$ |
| L121 | 4400   | 10.00  | 68.28 | 1  | 14    | $1.0 \times 10^{-6}$ |
| P123 | 5750   | 39.20  | 69.40 | 8  | 90    | $4.4 \times 10^{-6}$ |
| F127 | 12 600 | 200.45 | 65.17 | 22 | >100  | $2.8 \times 10^{-6}$ | a The average molecular weights provided by the manufacturer (BASF, Wyandotte, MI).
b The average numbers of EO and PO units were calculated using the average molecular weights.
c HLB values of the copolymers; the cloud points were determined by the manufacturer.
d Critical micellization concentration values were determined previously using pyrene probe (See, e.g., Kozlov et al., Macromolecules 33 (2000) 3305–3313).

COMPOSITIONS AND METHODS FOR TREATING AND PREVENTING CARDIOMYOPATHY AND HEART DISEASE

This application claims priority to U.S. Provisional Patent Application No. 60/656,570, filed Feb. 25, 2005, hereby incorporated by reference in its entirety.

This invention was made with government support under grant number AG015434 awarded by the National Institute of Health. The government has certain rights in the invention.

FIELD OF THE INVENTION

The present invention relates to compositions and methods for treating and preventing heart disease. In particular, the present invention provides compositions comprising poloxamers (e.g., poloxamer 188—P188) and methods of using the same for treating and preventing heart disease (e.g., in subjects with muscular dystrophy) and for treating cells and tissue damage caused by ischemia and cell death (e.g., for treating dystrophin-deficient cells (e.g., myocytes)).

BACKGROUND OF THE INVENTION

Heart failure is a chronic progressive disease. In the United States, there are 5 million patients with heart failure. Approximately 550,000 new cases are diagnosed and more that 285,000 deaths occur annually from heart failure indicating that the number of heart failure patients is on the rise.

Dystrophin-deficiency causes Duchenne muscular dystrophy (DMD) in humans, an inherited and progressive disease of striated muscle deterioration that frequently involves pronounced cardiomyopathy (See, e.g., Muntoni, Curr Opin Neurol 16, 577-83 (2003)). Heart failure accounts for an estimated 15% of the fatalities in DMD (See, e.g., Emery, A. E. H. in Duchenne Muscular Dystrophy (ed. Emery, A. E. H.) (Oxford University Press, Oxford, 2003)). Progress toward defining the molecular basis of disease in DMD has mostly come from studies on skeletal muscles, with comparatively little attention directed at cardiac muscle.

The pathophysiological mechanisms involved in cardiac myocytes are likely to differ significantly from skeletal myofibers, as underscored by significant cardiac disease in patients with truncated or reduced levels of dystrophin without skeletal muscle disease (See, e.g., Finsterer and Stollberger, Cardiology 99, 1-19 (2003)). Thus, several fundamental questions regarding the consequences of dystrophin-deficiency in cardiac muscle remain unanswered. Notably, it is unknown whether dystrophin-deficiency directly causes altered force transmission and/or membrane fragility in cardiac muscle at the single myocyte level.

There exists a need for new compositions and new methods for treating heart disease in general, as well as heart disease related to dystrophic cells, tissues and subjects, and for preventing and/or correcting the underlying bases of pathogenesis in subjects with heart disease (e.g., generally as well as in dystrophic subjects).

SUMMARY OF THE INVENTION

The present invention relates to compositions and methods for treating and preventing heart disease. In particular, the present invention provides compositions comprising poloxamers (e.g., poloxamer 188—P188) and methods of using the same for treating and preventing heart disease (e.g., in subjects with muscular dystrophy) and for treating cells and tissue damage caused by ischemia and cell death (e.g., for treating dystrophin-deficient cells (e.g., myocytes)).

Accordingly, in some embodiments, the present invention provides a method of treating a subject with diastolic dysfunction comprising administering to the subject a composition comprising a poloxamer under conditions such that diastolic dysfunction is improved in the subject. In some embodiments, the poloxamer is P188. In some embodiments, the subject is a human subject. The present invention is not limited by the type of subject treated with a composition comprising a poloxamer of the present invention. Indeed, a variety of subjects can be treated including, but not limited to, mice, dogs, pigs, and other non-human mammals. In some embodiments, the composition is administered via intravenous administration. The present invention is not limited by the route of administration of a composition comprising a poloxamer of the present invention. Indeed, a variety of routes can be used for administration including, but not limited to, intraarterial, subcutaneous, intraventricular, oral (e.g., via ingestion), or other route of administration. In some embodiments, treating prevents acute heart failure in said subject. In some embodiments, the improvement in diastolic dysfunction comprises an improvement in left ventricular function in the subject. In some embodiments, the improvement in left ventricular function comprises an improvement in baseline hemodynamic performance in the subject. In some embodiments, the improvement in diastolic dysfunction comprises an increase in left ventricular diastolic volume in the subject. In some embodiments, the subject is a dystrophin deficient subject. In some embodiments, the subject has Duchene's muscular dystrophy. In some embodiments the subject has diastolic heart failure or acute heart failure. In some embodiments, treating decreases susceptibility to calcium overload in heart tissue of the subject. In some embodiments, decreasing susceptibility to calcium overload in heart tissue of the subject comprises lowering intracellular $Ca^{+2}$ levels in cardiac myocytes of the subject. In some embodiments, lowering intracellular $Ca^{+2}$ levels in cardiac myocytes prevents remodelling or reverses remodelling of cardiac muscle tissue in the subject. In some embodiments, treating decreases cell contracture and/or cell death in the heart tissue of the subject. In some embodiments, the poloxamer is a purified and/or fractionated poloxamer. In some embodiments, the composition comprising a poloxamer is co-administered with one or more agents used for the treatment of heart disease including, but not limited to, a diuretic, a loop diuretic, a potassium sparing agent, a vasodilator, an ACE inhibitor, an angiotensin II antagonist, a positive inotropic agent, a phosphodiesterase inhibitor, a beta-adrenergic receptor antagonist, a calcium channel blocker, a nitrate, an alpha blocker, a central alpha antagonist, a statin, or a combination of these agents. In some embodiments, the composition and methods of the present invention find use in research and/or therapeutic (e.g., clinical therapy) applications.

The present invention also provides a method of increasing left ventricular diastolic volume in a dystrophin deficient subject comprising administering to the subject a composition comprising a poloxamer. In some embodiments, the poloxamer reduces intracellular calcium concentration in dystrophin-deficient cardiac myocytes in the subject. In some embodiments, reducing intracellular calcium concentration in dystrophin-deficient myocytes reduces the subject's susceptibility to calcium overload. In some embodiments, increasing left ventricular diastolic volume in the subject prevents acute cardiac failure in the subject. In some embodiments, improvement in left ventricular function comprises an improvement in baseline hemodynamic performance in the subject. In some embodiments, the dystrophin deficient subject is a human subject with Duchene's muscular dystrophy. In some embodiments, lowering intracellular calcium concentration in dystrophin-deficient cardiac myocytes prevents remodelling and/or reverses remodelling of cardiac muscle tissue in the subject. In some embodiments, the poloxamer is a purified poloxamer. In some embodiments, the poloxamer is a fractionated poloxamer. In some embodiments, the composition comprising a poloxamer is co-administered with one or more agents used for the treatment of heart disease including, but not limited to, a diuretic, a loop diuretic, a potassium sparing agent, a vasodilator, an ACE inhibitor, an angiotensin II antagonist, a positive inotropic agent, a phosphodiesterase inhibitor, a beta-adrenergic receptor antagonist, a calcium channel blocker, a nitrate, an alpha blocker, a central alpha antagonist, a statin, or a combination of these agents.

The present invention also provides a method of reducing calcium concentration in cardiac myocytes comprising administering a composition comprising a poloxamer to the cardiac myocytes. In some embodiments, the cardiac myocytes comprise dystrophin deficient cardiac myocytes. The present invention is not limited by the type of poloxamer administered to cardiac myocytes for altering calcium concentration therein. In some embodiments, the poloxamer is P188. In some embodiments, administering a composition comprising a poloxamer to the cardiac myocytes prevents cell contracture of the cardiac myocytes. In some embodiments, administering a composition comprising a poloxamer to the cardiac myocytes prevents cell death of the cardiac myocytes.

DESCRIPTION OF THE DRAWINGS

FIG. 4 shows micro-carbon fiber-based mechanical apparatus. A. Schematic of set-up. Bright field images (>590 nm) of the myocyte attached to a pair of carbon fibers (CF) on each end were recorded to measure the myocyte dimensions and sarcomere length. Programmed control of overall myocyte length was accomplished by a piezoelectric translator (PT). Tension development was detected by a force transducer (200 mV/mg) (FT). Emission fluorescence (510 nm) intensity, resulting from high speed switching of fluor excitation (340 and 380 nm), was detected by a photomultiplier tube (PMT). B. Photomicrographs of a single cardiac myocyte, attached with microcarbon fibers at each end, prior to passive stretch (top) and after stretch (bottom). Bar=20 µm. Expanded views show sarcomere length (1.8 µm (top), 2.2 µm (bottom)).

FIG. 8 shows (A) the backbone structure of a poloxamer and (B) examples of commercially available poloxamers useful in compositions and methods of the present invention.

Definitions

Figure 1:
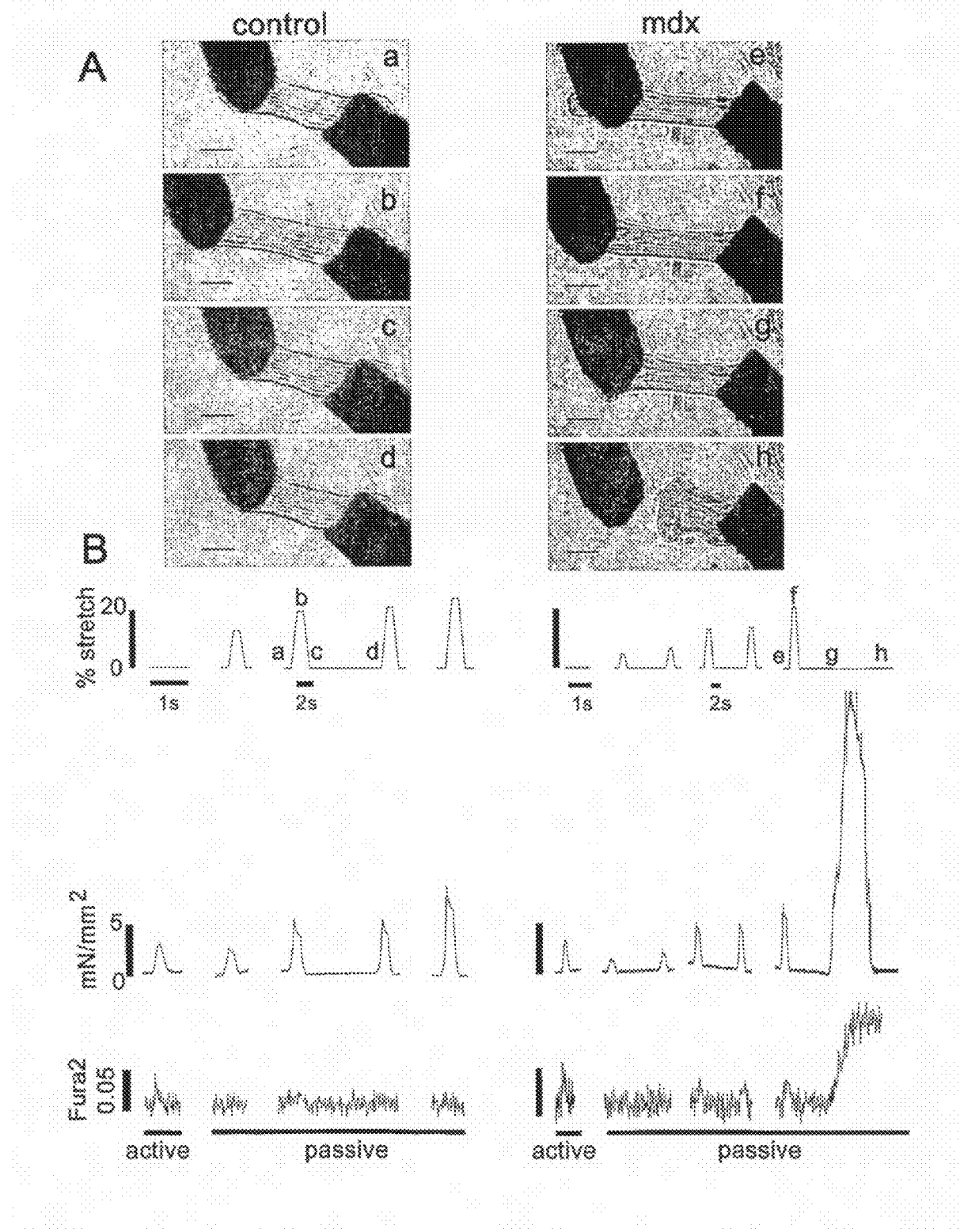
FIG. 1 shows representative recordings of active and passive tension, and $[Ca^{2+}]_i$ in single cardiac myocytes from control (left panels) and mdx (right panels) mice. A. Photomicrographs of single myocytes before (a, e), during (b, f), immediately after (c, g) and about 40 s after (d, h) a single passive stretch. Bar is 20 µm. B. Top traces are changes in myocyte length, starting at resting SL of 1.75-1.80 µm (0% stretch; isometric twitch) and extending to 2.1 µm (20% stretch and beyond). Traces marked a-h correspond to the sequence of cell stretch (a-h) shown in part A. Middle traces are tension recordings in response to stretch. Bottom traces are $[Ca^{2+}]_i$ (Fura2 ratios) during stretches. Left most traces are active isometric twitches. Passive recordings are in the absence of electrical stimulus. In mdx, after stretch (f) and return to rest length (g) myocyte became unstable, with massive increase in $[Ca^{2+}]_i$, hyper-contracture, and death (h).

As used herein, the term "signs and symptoms of heart disease" refers to signs and symptoms associated with heart disease (e.g., recognized by simple observation and, when combined with an individual's age and family history of heart disease, can lead to an accurate and early diagnosis of heart disease). Examples of signs and symptoms of heart disease include, but are not limited to, dyspnea, chest pain, palpitations, syncope, edema, cyanosis, and fatigue. A number of such symptoms are subject to quantitative analysis (e.g. palpitations, cyanosis, etc.). Other symptoms include diastolic dysfunction, decreased hemodynamic performance and decreased left ventricular-end diastolic volume. The term "wherein said symptoms are reduced" refers to a qualitative or quantitative reduction in detectable symptoms, including but not limited to an increase in hemodynamic performance and increased left ventricular-end diastolic volume.

As used herein, the phrase "under conditions such that signs and symptoms of heart disease are reduced" refers to any degree of qualitative or quantitative reduction in signs and symptoms of heart disease.

As used herein, the term "at risk for heart disease" refers to subjects (e.g., a segment of the world population, or research animals) that have an increased risk (i.e. over the average subject (e.g., person or research animal) for heart disease and can occur at any age.

As used herein, the term "therapeutic composition comprising a poloxamer" refers to compositions containing a poloxamer (e.g., P188) used for the treatment of heart disease. A therapeutic composition comprising a poloxamer may also comprise one or more other compounds or agents including, but not limited to, agent useful for the treatment of heart disease (e.g., ACE inhibitors, statins, beta blockers, and the like), other therapeutic agents, physiologically tolerable liquids, gels, carriers, diluents, excipients, salicylates, immunosuppressants, antibiotics, binders, fillers, preservatives, stabilizing agents, emulsifiers, and buffers.

As used herein, the terms "agent useful for the treatment of heart disease" and "agents useful for the treatment of heart disease" refer to any one or more agents currently used for the treatment of signs and symptoms of heart disease. These agents include, but are not limited to, a diuretic, a loop diuretic, a potassium sparing agent, a vasodilator, an ACE inhibitor, an angiotensin II antagonist, a positive inotropic agent, a phosphodiesterase inhibitor, a beta-adrenergic receptor antagonist, a calcium channel blocker, a nitrate, an alpha blocker, a central alpha antagonist, a statin, and combinations of two or more of these agents. Examples of these agents are provided herein. Also included within the meaning of these terms are agents that are being clinically evaluated (e.g., in a clinical trial) for efficacy in the treatment of signs and symptoms of heart disease.

As used herein, the terms "host," "subject" and "patient" refer to any animal, including but not limited to, human and non-human animals (e.g. rodents, arthropods, insects (e.g., Diptera), fish (e.g., zebrafish), non-human primates, ovines, bovines, ruminants, lagomorphs, porcines, caprines, equines, canines, felines, aves, etc.), that is studied, analyzed, tested, diagnosed or treated (e.g. administered therapeutically or prophylactically a composition comprising a poloxamer of the present invention). The terms "host," "subject" and "patient" are used interchangeably, unless indicated otherwise herein.

As used herein, the terms "therapeutically effective amount" and "effective amount" when used in reference to a composition comprising a poloxamer of the present invention refer to an amount (e.g., a dosage level) sufficient to effect beneficial or desired results (e.g., that are effective at treating or preventing signs and symptoms of heart disease). An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment (e.g., compositions of the present invention) to a subject (e.g., a subject or in vivo, in vitro, or ex vivo cells, tissues, and organs).

As used herein, the terms "co-administration" and "co-administering" refer to the administration of at least two agent(s) (e.g., a composition comprising a poloxamer and one or more other agents—e.g., a calcium channel blocker) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" or grammatical equivalents encompasses the improvement and/or reversal of the symptoms of heart disease. An agent that causes an improvement in any parameter associated with disease when used in screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or dysfunction (e.g., heart disease or diastolic dysfunction) as well as those in which a disease and/or dysfunction is to be prevented (e.g., using a prophylactic treatment of the present invention).

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., environmental conditions, hypertension, metabolic syndrome, etc.). Thus, it is not intended that the present invention be limited to any particular risk, nor is it intended that the present invention be limited to any particular type of heart disease.

As used herein, the term "suffering from disease" refers to a subject (e.g., a human) that is experiencing a particular disease. It is not intended that the present invention be limited to any particular signs or symptoms, nor disease. Thus, it is intended that the present invention encompass subjects that are experiencing any range of disease (e.g., from sub-clinical manifestation to full-blown disease) wherein the subject exhibits at least some of the indicia (e.g., signs and symptoms) associated with the particular disease.

As used herein, the terms "disease" and "pathological condition" are used interchangeably to describe a state, signs, and/or symptoms that are associated with any impairment of the normal state of a living animal or of any of its organs or tissues that interrupts or modifies the performance of normal functions.

The terms "compound" and "agents" refer to any chemical entity, pharmaceutical, drug, and the like that can be used to treat or prevent a disease, illness, sickness, or disorder of bodily function. Compounds comprise both known and potential therapeutic compounds. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of disease (e.g., heart disease).

DETAILED DESCRIPTION OF THE INVENTION

There are about 5 million patients within the United States that have heart disease, with approximately 2 million of this group having New York Heart Association Class III or class IV heart failure that encompasses the population with moderate to severe symptoms (See, e.g., American Heart Association. Heart Disease and Stroke Statistics-2006 Update, Dallas: AHA, 2006). About 22% of male and 46% of female heart attack victims will be disabled with heart failure within 6 years. This disease typically progresses from class III to IV over 3-10 years where the patient may be treated with pharmacological therapy including β-blockers, angiotensin II receptor type 1 blockers, angiotensin I converting enzyme inhibitors, calcium channel blockers, and vasodilators. As additional symptoms occur patients may require medical devices such as implantable pacemakers or defibrillators and possibly left ventricular assist devices (LVAD). With the possible exception of LVADs, these therapies prolong life but do not stop or reverse the deterioration of heart function. In the end-stages of this disease, patients are frequently hospitalized with dangerously low left ventricular ejection fraction and require intravenous (IV) inotropes to increase contractility of the heart muscle and diuretics to decrease fluid burden.

Several risk factors for heart failure appear to be increasing in the general population in the form of metabolic syndrome (e.g., hypertension, dyslipidemia, obesity and diabetes). An estimated 1 million 12-19 year old adolescents in the United States have metabolic syndrome or 4.2% overall. Forty seven million adults in the U.S. have metabolic syndrome or 23.7% overall. In the case of diabetes, left ventricular diastolic dysfunction may represent the first stage of diabetic cardiomyopathy (See, e.g., Raev, (1994) Diabetes Care 17: 633-639).

Diastolic dysfunction is a condition where abnormalities in mechanical function of the heart are present during diastole. It can be a prelude to diastolic heart failure characterized by signs and symptoms of heart failure in the presence of a preserved ejection fraction and abnormal diastolic function (See, e.g., Zile and Brutsaert (2002) Circ. 105: 1387-1393). These abnormalities are caused by decreased ventricular relaxation and/or increased ventricular stiffness. Diastolic dysfunction is very common. In a study by the Mayo Clinic, in the general population of Minnesota, 21% of adults over the age of 45 had mild diastolic dysfunction (See, e.g., Redfield et al., 2003 JAMA 289: 194-202)

Annual mortality from cardiomyopathy as either the primary cause of death or as a contributing factor is 54,700 (See, e.g., American Heart Association. Heart Disease and Stroke Statistics-2006 Update, Dallas: AHA, 2006). Eighty-seven percent of these cases are congestive or dilated cardiomyopathy (DCM). Of the patients with DCM, 50% are alive 5 years after initial diagnosis and 25% are alive after 10 years (Facts About Cardiomyopathy, NIH, NHLBI, 1995).

Approximately 1 in every 3500 males is affected with Duchenne Muscular Dystrophy (DMD) while Becker Muscular Dystrophy (BMD) is less common affecting approximately 1 in every 30,000 males. Both diseases are the result of mutations in the gene located on the X chromosome, at Xp21.1 that encodes dystrophin. In DMD, dystrophin is absent while in BMD it is either reduced or abnormal in size. Dystrophin is a structural protein that participates in cellular organization in muscle cells and promotes both myofibrillular and sarcolemma (muscle cell membrane) stability (See, e.g., Kaprielian and Severs, 2000 Heart Failure Reviews 5: 221-238). Cardiac disease in both DMD and BMD manifests as dilated cardiomyopathy and/or cardiac arrhythmia. It is seen in young patients with an incidence of 26% by the age of 6 years. Death occurs in these patients typically in their early to mid 20s. About 20% of DMD patients and 50% of BMD patients die from heart failure. Female carriers of DMD or BMD are also at risk for cardiomyopathy. The age of onset is unclear but is thought to be in the adult years. Cardiac involvement ranges from asymptomatic to severe heart failure.

It remains unclear just how heart failure arising from different etiologies relates to that associated with DMD. The loss of dystrophin and dystrophin-associated proteins in the membranes of cardiac myocytes from both human subjects and animal models is well documented and has recently been reviewed (See, e.g., Kawada et al., (2005). Pharmacol. Therap. 107: 31-43). These proteins form complexes that provide mechanical resistance to overexpansion of the sarcolemma. Loss of one of these proteins can result in disruption of the complex, membrane instability, muscle degeneration and eventually cardiomyopathy. It has been shown that there is a significant loss of dystrophin from the sarcolemma of cardiac myocytes in heart failure. This occurs in response to a diverse set of stressors including catecholamine administration, coronary ligation resulting in acute myocardial ischemia, and in chronic heart failure after myocardial infarction. The stressors can either be long term, effecting the structural remodeling of the heart, or immediate effecting the membrane stability and intracellular calcium levels. The increase in calcium concentration to high levels activates calcium-activated proteases (calpains) that, among other things, cleave dystrophin. This loss eventually leads to muscle degeneration, dilated cardiomyopathy (DCM; heart muscle disease associated with an enlarged and improperly functioning heart) and heart failure. This in turn may eventually lead to advanced heart failure.

In addition to the physical and emotional costs of heart failure, the financial costs are high. The annual costs are approximately $38 billion with 60% of that related to hospitalization. Annually, this accounts for 6.5 million hospital days. There has been a 174% increase in hospital discharges related to heart failure from 1979 to 2003 (See, e.g., American Heart Association. Heart Disease and Stroke Statistics-2006 Update, Dallas: AHA, 2006). Heart failure is the most common reason for hospitalization of Medicare beneficiaries (CDC, Heart Failure Fact Sheet). Thus, heart failure represents a growing medical challenge with 50% of patients having 3 or more co-morbidities, and the typical patient prescribed, on average, 6 medications. Seventy eight percent of subjects with some form of heart disease had at least 2 hospital admissions per year (See, e.g., English and Mastream, (1995) Crit. Care Nurs. Q. 18:1-6).

Notably, about 50% of heart failure patients (approximately 2 million subjects) have diastolic dysfunction. Thus, a major unmet medical need is for therapies that address diastolic dysfunction.

Accordingly, the present invention provides novel insights into the pathogenesis of cardiomyopathy and heart failure (e.g., related to diastolic dysfunction (e.g., in dystrophin-deficient myocytes and animals)) and compositions and methods for the treatment and prevention of the same and for research uses. Specifically, the present invention identifies that intact isolated dystrophin-deficient cardiac myocytes have reduced compliance and increased susceptibility to stretch-mediated calcium overload, leading to cell contracture and death. Furthermore, in some embodiments, the present invention provides methods of treating this calcium overload with a membrane sealant poloxamer (e.g., poloxamer 188—P188), a non-ionic co-polymer that can insert into artificial lipid monolayers and seal electroporated membranes. In some embodiments, treatment with a poloxamer (e.g., P188) reverses diastolic deficiencies at the myocyte- and organ-level (e.g., in dystrophic cells, tissues and subjects; See, Examples 3-6). In some embodiments, treatment with a poloxamer prevents acute heart failure in vivo.

Gene or cell-based approaches, demonstrated to have some efficacy in animal studies, are complicated in translating to humans. However, poloxamers are non-toxic and demonstrated safe in humans. Thus, in some embodiments, the present invention offers ready compositions for prophylactics and therapeutics for heart disease (e.g., caused by diastolic dysfunction (e.g., related to stretch mediated calcium overload (e.g., in DMD subjects and other diseases characterized by membrane instability))).

In particular, the present invention provides, in experimental datasets spanning single cardiac myocytes to whole animals, identification of the primary defect in dystrophic heart, and its correction by a chemical-based membrane repair strategy. First, a unique microcarbon fiber assay was employed that permitted the introduction of physiologically relevant sarcomere-length excursions on single living cardiac myocytes from normal and dystrophin-deficient (mdx) mice. Data generated during development of the present invention demonstrates that mdx myocytes, in response to passive distentions in cell length, have heightened susceptibility to intracellular calcium overload, causing myocyte hyper-contracture and death, indicating membrane fragility in response to physiological loading. The present invention also demonstrates that compositions (e.g., poloxamers (e.g., P188)) are capable of immediately restoring mdx myocyte compliance to that of control, and reverse mdx myocyte heightened susceptibility to calcium overload/cell contracture/death (See Examples 3-6). Accordingly, in some embodiments, the invention provides methods of protecting cells and subjects (e.g., humans, non-human mammals, etc.) from acute cardiac failure (and subsequent death) via administering to the subject a poloxamer (e.g., P188). In further embodiments, the invention provides treatments for diastolic dysfunction in a subject comprising administering (e.g., intravenous (IV) administration) to the subject (e.g., a dystrophic subject) a composition comprising a poloxamer (e.g., P188). Although an understanding of the mechanism is not necessary to practice the present invention and the present invention is not limited to any particular mechanism of action, in some embodiments, administration of a composition comprising a poloxamer (e.g., P188) produces improvements (e.g., immediate and/or sustained) in left ventricular function due to a return to normal of left ventricular diastolic volume.

The present invention demonstrates that in dystrophin-deficient hearts stretch-induced abnormal increases in $[Ca^{2+}]_i$ result in decreased compliance at the cellular level and lower diastolic volume in vivo (See Examples 2-4). Furthermore, the present invention demonstrates that the calcium influx results from a loss of membrane integrity, and that a composition comprising a poloxamer (e.g., P188) can correct these abnormalities.

Current therapeutic paradigms for DMD are focused on the expression of dystrophin, through exon skipping or viral transduction of truncated dystrophin, or other genes (e.g., utrophin or dysferlin) that limit the consequences of dystrophin deficiency (See, e.g., Gregorevic, et al., Nat Med 10, 828-34 (2004); Squire et al., Hum Mol Genet 11, 3333-44 (2002); Torrente et al., J Clin Invest 114, 182-95 (2004); Goyenvalle et al., Science 306, 1796-9 (2004)). These strategies are promising but are challenging due to the requisite targeting of all striated muscle in the body. The present invention provides a comparatively simple chemical-based alternative for treating DMD comprising administering to a subject with DMD a composition comprising a poloxamer. Although an understanding of the mechanism is not necessary to practice the present invention and the present invention is not limited to any particular mechanism of action, in some embodiments, administration of a poloxamer results in acute membrane stabilization and/or repair.

As demonstrated herein (e.g., in mouse and dog models of DMD; See Examples 5 and 6), administration of a poloxamer provides ready and immediate beneficial hemodynamic effects under both basal and stress conditions in dystrophic subjects. Currently, P188 is in phase III clinical trials for the treatment of vaso-occlusive crisis in sickle-cell anemia patients, having recently demonstrated the safety and non-toxicity of P188 in humans (See, e.g., Adams-Graves et al., Blood 90, 2041-6 (1997)). However, unlike the episodic course of sickle-cell anemia, DMD is a progressive disease, and effective poloxamer therapy, in some embodiments, utilizes chronic intravascular administration. Thus, the present invention utilizes membrane sealing poloxamers that represent a new class of therapeutic agents for preventing or limiting progressive damage to diastolic dysfunctional hearts (e.g., in DMD subjects), and for treating cardiomyopathies associated with defects in the dystrophin glycoprotein complex (See, e.g., Straub and Campbell, Curr Opin Neurol 10, 168-75 (1997)).

The present invention is not limited to any particular poloxamer for use in stabilizing the membrane of cardiac muscle cells in heart failure subjects (e.g., thereby increasing cellular compliance and improving heart function). In some preferred embodiments, P188 is used (e.g., in a composition (e.g., pharmaceutical composition) of the present invention). The present invention is not limited to use of P188. Indeed, any poloxamer that possesses similar characteristics and traits (e.g., biological effects) with those of P188 find use in the present invention including, but not limited to, P138, P237, P288, P124, P338, and P407.

P188 is one of a family of poloxamer molecules originally developed by BASF in the 1950s. It is a nonionic triblock co-polymer made of poly(ethylene oxide)$_{80}$-poly(propylene oxide)$_{30}$-poly(ethylene oxide)$_{80}$ (molecular mass≈8.4 Kda). The molecule has several names including PLURONIC F68, RheothRx, and FLOCOR.

Poloxamers (also termed PLURONIC block polymers, available from BASF Corp., Wyandotte, Mich.) generally comprise ethylene oxide (EO) and propylene oxide (PO) blocks arranged in a basic A-B-A structure: EO-PO-EO. This arrangement results in an am-phiphilic copolymer, in which the number of hydrophilic $EO_{(x)}$ and hydrophobic $PO_{(y)}$ units can be altered (See, e.g., Reeve, pgs. 231-249, in Handbook of Biodegradable Polymers, Harwood Academic Pub., Eds. Domb et al., (1997), hereby incorporated by reference in its entirety). The backbone structure of various poloxamers is shown in FIG. 8A. A list of selected PLURONIC copolymers available from BASF Corp. is shown in FIG. 8B. Copolymers with various x and y values are characterized by distinct hydrophilic-lipophilic balance (HLB). Poloxamers can be synthesized by sequential addition of PO and EO monomers in the presence of an alkaline catalyst, such as sodium or potassium hydroxide (See, e.g., Schmolka, J. Am. Oil Chem. Soc. 54 (1977) 110-116). The reaction is initiated by polymerization of the PO block followed by the growth of EO chains at both ends of the PO block. Anionic polymerization usually produces polymers with a relatively low polydispersity index (M/M).

In some embodiments, a composition comprising a poloxamer of the present invention comprises a purified and/or fractionated poloxamer (e.g., purified and/or fractionated using gel filtration or chromatographic fractionation (See, e.g., Emanuele et al., Expert Opin Investig Drugs. 1998; 7:1193-20, U.S. Pat. Nos. 6,977,045 and 6,761,824, each of which is hereby incorporated by reference in its entirety). In some embodiments, poloxamers are used that have admixtures (e.g., PO homopolymer and/or block copolymer admixtures) removed. In some embodiments, a poloxamer (e.g., polyoxypropylene/polyoxyethylene copolymer) is used that is optimized for improved biological activity (See, e.g., U.S. Pat. No. 6,747,064, hereby incorporated by reference in its entirety). In some embodiments, chemically modified forms of one or more poloxamers are utilized in the compositions and methods of the present invention. Chemical modifications of poloxamers include, but are not limited to, radiolabelling, acetylating, biotinylation, addition of a fluorophore, and other chemical modifications.

A variety of poloxamers can be used in (e.g., in a composition comprising a poloxamer) the present invention that possess similar characteristics and traits (e.g., biological effects) with those of P188 (e.g., based on characteristics described in FIG. 8b). These poloxamers include, but are not limited to, P138, P237, P288, P124, P338, and P407. In some embodiments, a poloxamer with a molecular weight of between 5000 and 9000 daltons is used (e.g., in a composition (e.g., pharmaceutical composition) of the present invention). In some embodiments, a poloxamer with a molecular weight of between 9000 and 12000 daltons is used (e.g., in a composition (e.g., pharmaceutical composition) of the present invention). In some embodiments, a poloxamer with a molecular weight of between 12000 and 15000 daltons is used. A poloxamer with a molecular weight below 5000 or greater than 15000 daltons may also find use in the present invention (e.g., in a composition (e.g., pharmaceutical composition) of the present invention).

In some embodiments, a poloxamer with a polyoxyethylene content greater than 50% is used (e.g., in a composition (e.g., pharmaceutical composition) of the present invention). In some embodiments, a poloxamer with a polyoxyethylene content between 50 and 60% is used. In some embodiments, a poloxamer with a polyoxyethylene content between 60 and 70% is used. Poloxamers with a polyoxyethylene content below 50% and above 70% may also find use in the present invention (e.g., in a composition (e.g., pharmaceutical composition) of the present invention).

Some common biological uses of P188 include use as a stool softener in several commercially available laxatives, as an ingredient in cosmetics and as an emulsifier for pharmaceutical agents. It is a powerful surfactant. P188 has been shown to insert into lipid monolayers (See, e.g., Maskarinec et al., 2002 Biophys. J. 82: 1453-1459). It has many biological effects in vivo including the repair of electrically damaged cell membranes (See, e.g., Lee et al., (1992) Proc. Natl. Acad. Sci. USA 89: 4524-4528), in controlled drug delivery, for sensitizing tumors to chemotherapy (See, e.g., Kabanov et al., Adv Drug Deliv Rev 2002, 54, 759-779), and for delivery of gene therapies, among others. Additionally, P188 was shown to have an effect on blood flow and viscosity as well as platelet adhesiveness. (See, e.g., Grover et al., (1969) Circ. 39 and 40: I249, (Suppl. I)). It was developed as a therapeutic agent under the name of RheothRx by Glaxo Welcome (See, e.g., Adams-Graves et al., (1997), Blood 90: 2041-2046) and by CytRx under the name of FLOCOR for vaso-occlusive crisis in sickle cell disease and has been in phase III clinical trials (See, e.g., Emanuele, (1998) Expert Opin. Investig. Drugs 7:1193-1200). It was also in Phase III trials to assess thrombolytic activity in patients with acute myocardial infarction (MI) (CORE), with mixed results (Schaer et al., (1996) Circ. 94: 298-307; Chareonthaitawe et al., (2000) Heart 84: 142-148). It has been in Phase II trials as an adjunct to primary percutaneous transluminal coronary angioplasty for acute MI (See, e.g., O'Keefe, et al., 1996 Am. J. Cardiol. 78: 747-750). Thus, the present invention contemplates use of poloxamers (e.g., P138, P237 and P288) that enjoy similar characteristics and biological effects to those of P188 (e.g., to treat and/or prevent heart failure (e.g., caused by diastolic dysfunction)).

P188 is safe when given acutely for up to 72 hr (See, e.g., Adams-Graves et al., (1997), Blood 90: 2041-2046) and is well tolerated in children and adults upon repeated exposure (See, e.g., Gibbs and Hagemann, 2004 Ann. Pharmacother. 38: 320-324). The most significant adverse effect in studies with RheothRx was renal dysfunction but this was not seen with the more highly purified form FLOCOR. The most frequently experienced adverse effects were pain, injection site abnormalities and nausea. It has a half-life in plasma of 7.5 hr in rodents and 18 hr in human subjects. Pharmacokinetic studies have shown that <5% of purified poloxamer is metabolized. A single metabolite of higher molecular weight and slower clearance has been detected (See, Gibbs and Hagemann, 2004 Ann. Pharmacother. 38: 320-324). Renal clearance is the primary route of elimination.

The present invention provides that a composition comprising a poloxamer (e.g., P188) can be used as a first-in-class therapy for heart disease. In some embodiments, a composition comprising a poloxamer (e.g., P188) provides additive or synergistic benefits when administered with one or more compositions (e.g, pharmaceuticals, drugs, etc.) used currently for heart disease.

In some embodiments, compositions of the present invention are used to treat dystrophin deficient myocytes (e.g., that develop more tension, compared to normal cardiac myocytes, when stretched to sarcomeric lengths physiologically relevant to diastole). In some embodiments, compositions of the present invention (e.g., comprising a poloxamer) are used to treat or prevent cardiac muscle cells from becoming unstable (e.g., that display fibrillations, calcium overload, contracture and/or cell death). For example, in some embodiments, a composition comprising a poloxamer of the present invention can be used to increase cellular compliance and decrease intracellular $Ca^{+2}$ to control levels in unstable cardiac myocytes. Although an understanding of the mechanism is not necessary to practice the present invention and the present invention is not limited to any particular mechanism of action, in some embodiments, treating unstable cardiac myocytes with a composition comprising a poloxamer of the present invention (e.g., administrating a composition comprising a poloxamer to myocytes) alters (e.g., neutralizes the detrimental effect, and/or, reconstitutes (e.g., repairs)) small tears in the sarcolemma.

In vivo studies of heart function revealed that intravenous infusion of poloxamer into subjects with diastolic heart abnormalities (e.g., mdx mice) improved baseline hemodynamic performance, including an increase in left ventricular end-diastolic volume (See, Examples 3-6). Thus, in some embodiments, the present invention provides a method of increasing left ventricular-end diastolic volume in a subject (e.g., a subject suffering from diastolic dysfunction) comprising providing a subject and administering to the subject a composition comprising a poloxamer (e.g., P188, or equivalent thereof). In some embodiments, compositions and methods of the present invention are used to increase left ventricular-end diastolic volume in subjects with heart failure (e.g., end-stage or symptomatic heart failure (e.g., in subjects with muscular dystrophy, or, heart failure generally)). Although an understanding of the mechanism is not necessary to practice the present invention and the present invention is not limited to any particular mechanism of action, in some embodiments, administration of a poloxamer to a subject lowers intracellular $Ca^{+2}$ levels in cardiac myocytes of the subject, thereby preventing remodelling of cardiac muscle tissue and/or reversing remodelling of cardiac tissue due to heart failure.

The present invention is not limited by the type of heart failure treated. Indeed, any heart failure comprising diastolic defects (e.g., defects of left ventricular-end diastolic volume) can be treated with the compositions and methods of the present invention. In some embodiments, the diastolic defect results from cardiomyopathy. The cardiomyopathy may be any one or more of a diverse group of diseases characterized by myocardial dysfunction. Cardiomyopathies are categorized hemodynamically into dilated, hypertrophic, restrictive and obliterative cardiomyopathy, and can be of known or idiopathic etiology. Among the etiologies of dilated cardiomyopathy are pregnancy, drugs and toxins, such as alcohol, cocaine and chemotherapeutic agents (e.g., doxorubicin and daunorubicin, dactinomycin, dacarbazine, cyclophosphamide, mitomycin, and anthracycline), and infectious and autoimmune processes. Hypertrophic cardiomyopathy is hereditary in more than 50% of cases and has a distinctive pattern of myocardial hypertrophy (e.g., thickening of muscle) usually with a pattern of asymmetrical thickening of the interventricular septum (also called asymmetrical septal hypertrophy). Restrictive cardiomyopathies are usually the product of an infiltrative disease of the myocardium, such as amyloidosis, hemochromatosis or a glycogen storage disease, and may also be seen in certain diabetic patients. Obliterative cardiomyopathy can be caused by endomyocardial fibrosis and hypereosinophilic syndrome. A common complication of all of the cardiomyopathies is progressive congestive heart failure.

Congestive heart failure is often defined as the inability of the heart to deliver a supply of oxygenated blood sufficient to meet the metabolic needs of peripheral tissues at normal filling pressures. Chronic congestive heart failure can result as a consequence of coronary artery disease, cardiomyopathy, myocarditis, aortic stenosis, hypertension, idiopathic asymmetrical septal hypertrophy, coarctation of the aorta, aortic regurgitation, mitral regurgitation, left-to-right shunts, hypertrophied muscle, pericardial tamponade, constrictive pericarditis, mitral stenosis, left atrial mzxoma, left atrial thrombus, cortriatriatum and numerous other conditions. Congestive heart failure is generally distinguished from other causes of inadequate oxygen delivery (e.g., circulatory collapse from hemorrhage or other causes of severe volume loss, congestion caused by fluid overload and high-output failure caused by increased peripheral demands which occurs in conditions such as thyrotoxicosis, arteriovenous fistula, Paget's disease and anemia). Therapy for congestive heart failure has typically focused on treating the underlying etiology and the symptoms of fluid overload and heart failure. Chronic congestive heart failure that persists after correction of reversible causes can be treated with diuretics (e.g., including, but not limited to, thiazides such as chlorothiazide and hydrochlorothiazide), loop diuretics (e.g., including, but not limited to, ethacrynic acid, furosemide, torsemide and bumetanide), potassium sparing agents (e.g., including, but not limited to, spironolactone, triamterene and amiloride), and others agents (e.g., including, but not limited to, metolazone and other quinazoline-sulfonamides), vasodilators (e.g., nitroglycerin, isosorbide dinitrate, hydralazine, sodium nitroprusside, prostacyclin, captopril, enalapril, lisinopril, quinapril and losartan), positive inotropic agents (e.g., digitalis or digoxin), beta blockers, or combinations of one or more of these agents.

Compositions and methods of the present invention can be used to treat multiple types of heart failure including, but not limited to, chronic heart failure (e.g., long-term congestive heart failure (e.g., congestive heart failure persisting more than two weeks, or more than three weeks, or more than one month, or more than two months, more than three months, or more)), heart failure that persists after correction of reversible causes, and heart failure not immediately associated with an acute myocardial infarction or an acute infectious process. In addition, heart disease caused by congenital heart defects (e.g., that may result in congestive heart failure or cyanotic heart disease (e.g., pulmonary atresia, total anomalous pulmonary venous return, ventricular septal defect, hypoplastic left heart syndrome, double outlet right ventricle, right pulmonary artery stenosis, interrupted aortic arch, Ebsteins's anomaly, tetralogy of Fallot, atrioventricular canal, transposition of the great arteries and truncus arteriosus) may also be treated with compositions and methods of the present invention.

Accordingly, the present invention is not limited by the type of subject administered a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have or are likely to suffer from heart disease (e.g., caused by diastolic dysfunction (e.g., a subject with DMD)). In some embodiments, the subjects are non-human mammals (e.g., pigs, cattle, goats, horses, sheep, or other livestock; or mice, rats, rabbits or other animal commonly used in research settings).

The present invention further provides pharmaceutical compositions (e.g., comprising a poloxamer described herein). A composition comprising a poloxamer of the present invention can be used therapeutically (e.g., to correct diastolic dysfunction) or as a prophylactic (e.g., to prevent signs or symptoms of heart disease (e.g., diastolic dysfunction)). A composition comprising a poloxamer of the present invention can be administered to a subject via a number of different delivery routes and methods.

In preferred embodiments, a composition comprising a poloxamer of the present invention is administered via intravenous (IV) administration. In some embodiments, a composition of the present invention may be administered one or more times a day for several days. In some embodiments, a composition of the present invention may be administered one or more times a day for more than one week. In some embodiments, a composition of the present invention may be administered one or more times a day for two or more weeks. In some embodiments, a composition of the present invention may be administered one or more times a day for one or more months, two or more months, four or more months, eight or more months, or for more than a year. In preferred embodiments, a composition of the present invention is administered (e.g., via chronic administration (e.g., administered one, two, three or more times a week in a physician's office for a duration (e.g., over a period of weeks, months or years) that is sufficient to increase heart function and/or stop progression of disease and/or reverse remodelling of heart tissue (e.g., by lowering and maintaining intracellular calcium levels at normal levels). The present invention is not limited by intravenous administration. Indeed, any method of administration that introduces a composition of the present invention into the vasculature is contemplated to be useful as a delivery means. For example, in some embodiments, a composition of the present invention is administered via parenteral administration. Examples of parenteral administration include intravenous, intraarterial, subcutaneous, intraperitoneal, intramuscular injection or infusion, intrathecal or intraventricular administration.

Compositions and formulations for parenteral, IV, or other route of administration may include sterile aqueous solutions that may also contain buffers, diluents and other suitable additives such as, but not limited to, penetration enhancers, carrier compounds and other pharmaceutically acceptable carriers or excipients.

A composition of the present invention may be formulated for administration by any route, such as intravenous, or other route described herein. In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for IV, parenteral, mucosal, subcutaneous, intramuscular, intraperitoneal, intravenous, oral (e.g., via ingestion) or administration via other routes may be found in Remington: The Science and Practice of Pharmacy, Mack Publishing Company, Easton, Pa., 19th edition, 1995.

In additional preferred embodiments, a composition of the present invention is administered in an amount (e.g., a dose) that is sufficient to increase heart function and/or stop progression of disease and/or reverse remodelling of heart tissue (e.g., by lowering and maintaining intracellular calcium levels at normal levels). The present invention is not limited to any particular dose. Indeed, the desired dose may vary depending upon the subject being treated (e.g., the age, health status, and type and/or degree of heart disease being treated).

In some embodiments, it is expected that each dose (e.g., of a composition comprising a poloxamer (e.g., administered to a subject to prevent or treat heart disease (e.g., caused by diastolic dysfunction)) comprises between 100-200 mg of poloxamer per kg weight of the subject being treated. In some embodiments, each dose comprises between 200-400 mg of poloxamer per kg weight of the subject being treated. In some embodiments, each dose comprises between 400-500 mg of poloxamer per kg weight of the subject being treated. In some embodiments, each dose comprises 500-2000 mg of poloxamer per kg weight of the subject being treated. In some embodiments, each dose comprises less than 100 mg of poloxamer per kg weight of the subject being treated. In some embodiments, each dose comprises more than 2000 mg of poloxamer per kg weight of the subject being treated. An optimal amount for a particular administration can be ascertained by standard studies involving observation of diastolic function and other biological responses (e.g., blood oxygen saturation) in subjects.

In some embodiments, it is expected that each dose (e.g., of a composition comprising a poloxamer that is administered to a subject (e.g., a human subject)) is by weight 30% poloxamer. However, a dose may comprise more or less than this amount of poloxamer. For example, in some embodiments, a dose may comprise between 30-40% poloxamer by weight. In some embodiments, a dose may comprise between 40-50% w/w poloxamer. In some embodiments, a dose may comprise 50-60% w/w poloxamer. In some embodiments, a dose may comprise greater than 60% poloxamer by weight.

In some embodiments, pharmaceutical preparations comprising a poloxamer are formulated in dosage unit form for ease of administration and uniformity of dosage. Dosage unit form, as used herein, refers to a physically discrete unit of the pharmaceutical preparation appropriate for the subject undergoing treatment (e.g., administration of a composition of the present invention). Each dosage should contain a quantity of the compositions comprising a poloxamer calculated to produce the desired response (e.g., increase in diastolic pressure). Procedures for determining the appropriate dosage unit, in addition to being described herein, are well known to those skilled in the art.

Dosage units may be proportionately increased or decreased based on several factors including, but not limited to, the weight, age, and health status of the subject. In addition, dosage units may be increased or decreased based on the response of the subject to the treatment (e.g., diastolic pressure gains or losses).

In certain embodiments of the invention, compositions may further comprise one or more alcohols, zinc-containing compounds, emollients, humectants, thickening and/or gelling agents, neutralizing agents, and surfactants. Water used in the formulations is preferably deionized water having a neutral pH.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the poloxamer of the formulation.

The present invention also includes methods involving co-administration of a composition comprising a poloxamer with one or more additional active agents (e.g., agents that are known in the art for treating or preventing heart failure). Indeed, it is a further aspect of this invention to provide methods for enhancing prior art treatment methods and/or pharmaceutical compositions by co-administering a composition of the present invention. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered can be any of the well-known agents in the art, including, but not limited to, those that are currently in clinical use.

It is contemplated that the administration of a composition comprising a poloxamer may be co-administered with one or more known therapeutic agents for treating heart disease. For example, agents that are known in the art for treating heart disease include, but are not limited to, diuretics (e.g., thiazides such as chlorothiazide, hydrochlorothiazide and metolazone), loop diuretics (e.g., ethacrynic acid, furosemide, torsemide and bumetanide and their congeners), potassium sparing agents (e.g., spironolactone, canrenone, triamterene and amiloride, and others agents such as metolazone and other quinazoline-sulfonamides), vasodilators (e.g., nitrovasodilators (e.g., nitroglycerin, isosorbide dinitrate, and sodium nitroprusside), hydralazine, prostacyclin, ACE inhibitors (e.g., captopril, enalapril, lisinopril, quinapril and ramipril), and angiotensin II antagonists (e.g., losartan), positive inotropic agents (e.g., cardiac glycosides (e.g., digitalis or digoxin)), phosphodiesterase inhibitors (e.g., amrinone and milrinone), beta-adrenergic receptor antagonists (e.g., beta blockers such as propanolol, metoprolol, atenolol, pindolol, acebutolol, labetalol, carvedilol and celiprolol), or combinations of these measures (See, e.g., Goodman and Gilman, Ch. 34, The Pharmacological Basis of Therapeutics, McGraw Hill, N.Y. (1996), incorporated by reference herein).

Current therapeutic recommendations for the treatment of diastolic heart failure are based on disease-oriented evidence, including pathophysiology, extrapolation of knowledge about other aspects of cardiovascular disease, data from small studies, and expert opinion. Evidence-based guidelines from the American College of Cardiology/American Heart Association (ACC/AHA) and the Institute for Clinical Systems Improvement (ICSI) provide some information regarding treatment regimens (See, e.g., Hunt et al., Circulation 2001; 104:2996-3007; Institute for clinical systems improvements. Health care guidelines. January 2002: 1-71).

For example, lifestyle modifications are recommended to reduce the risk of all forms of cardiovascular disease. Measures include weight loss, smoking cessation, dietary changes, and exercise. Identification and treatment of co-morbid conditions, such as high blood pressure, diabetes, and hypercholesterolemia, are important in reducing the risk of subsequent heart failure.

A composition comprising a poloxamer of the present invention may be co-administered with one or more pharmaceutical agents used to treat diastolic heart failure. For example, pharmacologic treatment of diastolic heart failure is directed at normalizing blood pressure, promoting regression of left ventricular hypertrophy, preventing tachycardia, treating symptoms of congestion, and maintaining atrial contraction (See, e.g., Hunt et al., Circulation 2001; 104:2996-3007; Institute for clinical systems improvements. Health care guidelines. January 2002: 1-71; Zile and Brutsaert, Circulation 2002; 105: 1503-8). Treatment with diuretics and vasodilators often is important to reduce pulmonary congestion. However, caution is required to avoid excessive diuresis, which can decrease preload and stroke volume. Subjects with diastolic dysfunction are sensitive to volume changes and preload. The potential benefits of beta blockers stem from their ability to decrease heart rate, increase diastolic filling time, decrease oxygen consumption, lower blood pressure, and cause regression of left ventricular hypertrophy. One group is evaluating the effect of the beta blocker nebivolol in the treatment of elderly patients with diastolic heart failure (See, e.g., Shibata et al., Int J Cardiol 2002; 86:77-85). Accordingly, in some embodiments, a composition comprising a poloxamer (P188) is co-administered with a diuretic and/or a vasodilator and/or a beta blocker to a subject in order to treat or prevent heart disease (e.g., disease caused by diastolic dysfunction) in the subject.

The present invention is not limited by the type of diuretic co-administered with a composition comprising a poloxamer of the present invention. Indeed, a variety of diuretics can be co-administered including, but not limited to, amiloride (MIDAMOR), bumetanide (BUMEX), chlorothiazide (DIURIL), furosemide (LASIX), hydrochlorothiazide (ESDRIX), indapamide (LOZOL), and spironolactone (ALDACTONE).

Similarly, the present invention is not limited by the type of beta blocker co-administered with a composition comprising a poloxamer of the present invention. Indeed, a variety of beta blockers can be co-administered including, but not limited to, acebutolol (SECTRAL), atenol (TENORMIN), betaxolol (KERLONE), bisoprolol/hydrochlorothiazide (ZIAC), bisoprolol (ZEBETA), carteolol (CARTROL), metoprolol (LOPRESSOR, TOPROL XL), nadolol (CORGRAD), propranolol (INDERAL), sotolol (BETAPACE), and timolol (BLOCADREN).

The multiple benefits of angiotensin-converting enzyme (ACE) inhibitors in the treatment of cardiovascular disease make these agents promising therapeutic agents for the treatment of heart disease (e.g., caused by diastolic dysfunction). ACE inhibitors cause regression of left ventricular hypertrophy, decrease blood pressure, and prevent and/or modify cardiac remodelling. Accordingly, in some embodiments, a composition comprising a poloxamer (e.g., P188) is co-administered with an ACE inhibitor to a subject in order to treat or prevent heart disease in the subject (e.g., disease caused by diastolic dysfunction).

Examples of ACE inhibitors that find use in the compositions and methods of the present invention include, but are not limited to, Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]-amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); R.sub.O 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; rentiapril (fentiapril, Santen) disclosed in Clin. Exp. Pharmacol. Physiol. 10:131 (1983); indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344, 949 and CI 925 (Warner-Lambert) ([3S-[2[R(*)R(*)]] 3R(*)]-2-[2-[[1-(ethoxy-carbonyl)-3-phenylpropyl] amino[-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983), each of which is hereby incorporated by reference in its entirety.

Diastolic heart failure can also be treated with calcium channel blockers (e.g., verapamil and diltiazem), and beta-adrenergic receptor blockers. In cases of pulmonary congestion or ischemia, patients may also receive diuretics or nitrates, respectively.

Calcium channel antagonists can improve diastolic function directly, by attenuating calcium homeostasis, or indirectly, by reducing blood pressure, reducing or preventing myocardial ischemia, promoting regression of left ventricular hypertrophy, slowing heart rate (e.g., using verapamil and/or diltiazem), and improving left ventricular filling parameters. Accordingly, in some embodiments, a composition comprising a poloxamer (P188) is co-administered with a calcium channel blocker (e.g., verapamil and diltiazem) and/or beta-adrenergic receptor blocker in order to treat or prevent heart disease (e.g., disease caused by diastolic dysfunction) in the subject.

Examples of calcium channel blockers include, but are not limited to, amlodipine (NORVASC), bepridil (VASCOR), diltiazem (CARDIZEN, TIAZAC), felodipine (PLENDIL), nifedipine (ADALAT, PROCARDIA), nimodipine (NIMOTOP), nisoldipine (SULAR), and verapamil (CALAN, ISOPTIN, VERELAN)

Verapamil has been shown by objective criteria to improve diastolic function, ameliorate symptoms, and increase exercise tolerance. In a five-week, double-blind cross-over trial conducted in 1990 by J. F. Setaro and colleagues, 20 elderly men with isolated diastolic dysfunction were treated with verapamil or placebo. In those receiving the drug, symptoms improved, exercise time increased 33%, peak left ventricular filling rate increased 30%, and heart rate decreased 10% ($p<0.05$ for all).

In some embodiments, a composition comprising a poloxamer (P188) is co-administered with an angiotensin-2 receptor antagonist and/or an alpha blocker and/or a central alpha agonist and/or a statin order to treat or prevent heart disease (e.g., disease caused by diastolic dysfunction) in the subject.

Examples of angiotensin-2 receptor antagonists that find use in the present invention include, but are not limited to, candesartan (ATACAND), eprosartan (TEVETEN), irbesartan (AVAPRO), losartan (COZAAR), telmisartan (MICARDIS), and valsartan (DIOVAN). Examples of alpha blockers that find use in the present invention include, but are not limited doxazosin mesylate (CARDURA), prazosin hydrochloride (MINIPRESS), prazosin and polythiazide (MINIZIDE), and terazosin hydrochloride (HYTRIN). Examples of central alpha agonists that find use in the present invention include, but are not limited to, clonidine hydrochloride (CATAPRES), clonidine hydrochloride and chlorthalidone (CLORPRES, COMBIPRES), Guanabenz Acetate (WYTENSIN), Guanfacine hydrochloride (TENEX), Methyldopa (ALDOMET), Methyldopa and chlorothiazide (ALDOCLOR), and methyldopa and hydrochliorothiazide (ALDORIL). Examples of statins that find use (e.g., for co-administration with a composition comprising a poloxamer to a subject (e.g., in order to treat and/or prevent heart disease in the subject)) in the present invention include, but are not limited to, atorvastatin (LIPITOR), fluvastatin (LESCOL), lovastatin (MEVACOR), pravastatin (PRAVACHOL), rosuvastatin calcium (CRESTOR), and simvastatin (ZOCOR).

EXPERIMENTAL

The following examples are provided in order to demonstrate and further illustrate certain preferred embodiments and aspects of the present invention and are not to be construed as limiting the scope thereof.

Example 1

Materials and Methods

Animals. Control (C57BL/10 SnJ) and mdx (C57BL/10 ScSn-mdx) mice obtained from Jackson Laboratories were maintained in barrier isolation facilities at the University of Michigan. The procedures used in this study were approved by the University of Michigan Committee on the Use and Care of Animals.

Measurement of single cardiac myocyte length, tension, and intracellular $[Ca^{2+}]$ ($[Ca]_i$) The methods for isolating mouse adult cardiac myocytes have been reported (See, e.g., Coutu et al., Circ Res 94, 1235-41 (2004)). Briefly, the acutely isolated single myocytes were transferred to an experimental chamber containing a silicon-coated glass bottom and platinum electrodes mounted on the sides to electrically stimulate the myocytes, which was mounted on the stage of an inverted microscope (TE300, Nikon; objective 40×). The chamber was kept at 37° C. with a thermoelectric device. Length/tension/$[Ca^{2+}]_i$ measurement system of membrane intact cardiac myocytes was developed with modifications from a previously reported method (See, e.g., Yasuda, S. I. et al., Am J Physiol Heart Circ Physiol 281, H1442-6 (2001)) using a pair of microcarbon fibers. One fiber was connected to a sensitive force transducer system (200 mV/mg, Aurora Scientific Inc., Canada), and the other was connected to a piezoelectric translator (P-173, PI Polytec) to control myocyte length. The carbon fibers used in this study were rigid (diameter, 40 µm; compliance, 0.02 m/N), and not altered by the active and passive tensions produced by single cardiac myocytes. Tension signal from the force transducer and length signal applied to the piezoelectric translator were recorded at 1000 Hz sampling rate with an analog-to-digital recording system (Accura 100, Nicolet). Video recordings of the cardiac myocytes were digitized to measure cell extension and sarcomere length via images on a computer screen. For measurement of $[Ca^{2+}]_i$ myocytes were incubated with 5 µM Fura-2-acetoxy-methyl (AM) ester (Molecular Probes) and 0.02% Pluronic F127 (Molecular Probes) for 4 minutes at 37° C. Fura-2 excitation was sampled at 100 Hz using a microscope-based fluorescence spectrometer (Photon Technology International). $[Ca^{2+}]_i$ was determined by a previously established method (See, e.g., Grynkiewicz et al., J Biol Chem 260, 3440-50 (1985)) after subtracting background fluorescence intensity. The effect of P188 (0.15 mM in extracellular buffer) (See, e.g., Lee et al., Ann N Y Acad Sci 888, 266-73 (1999)) and nifedipine (1 µM) on passive tension-extension characteristics and $[Ca]_i$ of control and mdx single cardiac myocytes was investigated. In another procedure, cardiac myocytes were stretched during the rising phase of twitch tension (lengthening contraction). Upon restoring SL, isometric twitch tension was compared post/pre stretch.

In Vivo Cardiac Hemodynamic. Murine pressure volume loops were acquired by methods outlined previously (See, e.g., Michele et al., Circ Res 91, 255-62 (2002)). Briefly, anesthetized mice were ventilated with 2% isoflourane and 98% oxygen. A thoracotomy and pericardiotomy were performed, and pressure-volume catheter was inserted into the LV via an apical stab. Prior to catheter insertion, mice received an I.V. infusion of ≈150 µl of 10% human albumin with and without P188 at a rate of ≈200 µl/kg/min. Following the collection of baseline hemodynamic data, dobutamine was infused at a dose of 42 µg/kg/min. The dose of P188, 460 mg/kg, was shown to be effective in mitigating skeletal muscle damage following electrocution (See, e.g., Lee et al., Proc Natl Acad Sci U S A 89, 4524-8 (1992)). Acute cardiac failure was defined to occur when LV systolic pressure dropped below 60 mmHg, as below this level, rapid decompensation and death were frequent occurrences. Following the 30-minute dobutamine challenge or the development of acute cardiac failure, volume measurements were calibrated as previously described (See, e.g., Michele et al., Circ Res 91, 255-62 (2002)).

Example 2

Micro-Carbon Fiber-Based Mechanical Apparatus

The present invention provides a unique micro-carbon fiber technique (See FIG. 4) that enables for the first time the simultaneous assessment of force and intracellular calcium concentrations of isolated membrane intact myocytes under physiologically relevant mechanical loading. Using this technology, single, membrane intact, adult cardiac myocytes from dystrophin deficient (mdx) and control mice were passively stretched over a physiologically relevant range of sarcomere lengths (1.75 to 2.2 µm; (See, e.g., Rodriguez, et al., Am J Physiol 263, H293-306 (1992))) and passive tension and $[Ca^{2+}]_i$ were recorded. FIG. 1A shows photomicrographs of control and mdx myocytes at different stages during the stretch protocol. FIG. 1B shows representative simultaneous recordings of length, tension, and Fura-2 ratio of single cardiac myocytes from a control and mdx mouse. In FIG. 1B, the traces on the left are the active twitch tension and calcium transient during an electrically stimulated isometric contraction at a resting sarcomere length (SL) of 1.75-1.8 µm.

Remaining traces are tension and calcium recordings during passive stretching of the myocyte from a resting SL of 1.75 µm (0% stretch) to a physiologically relevant diastolic SL of 2.0 to 2.2 µm (20% stretch).

Figure 2:
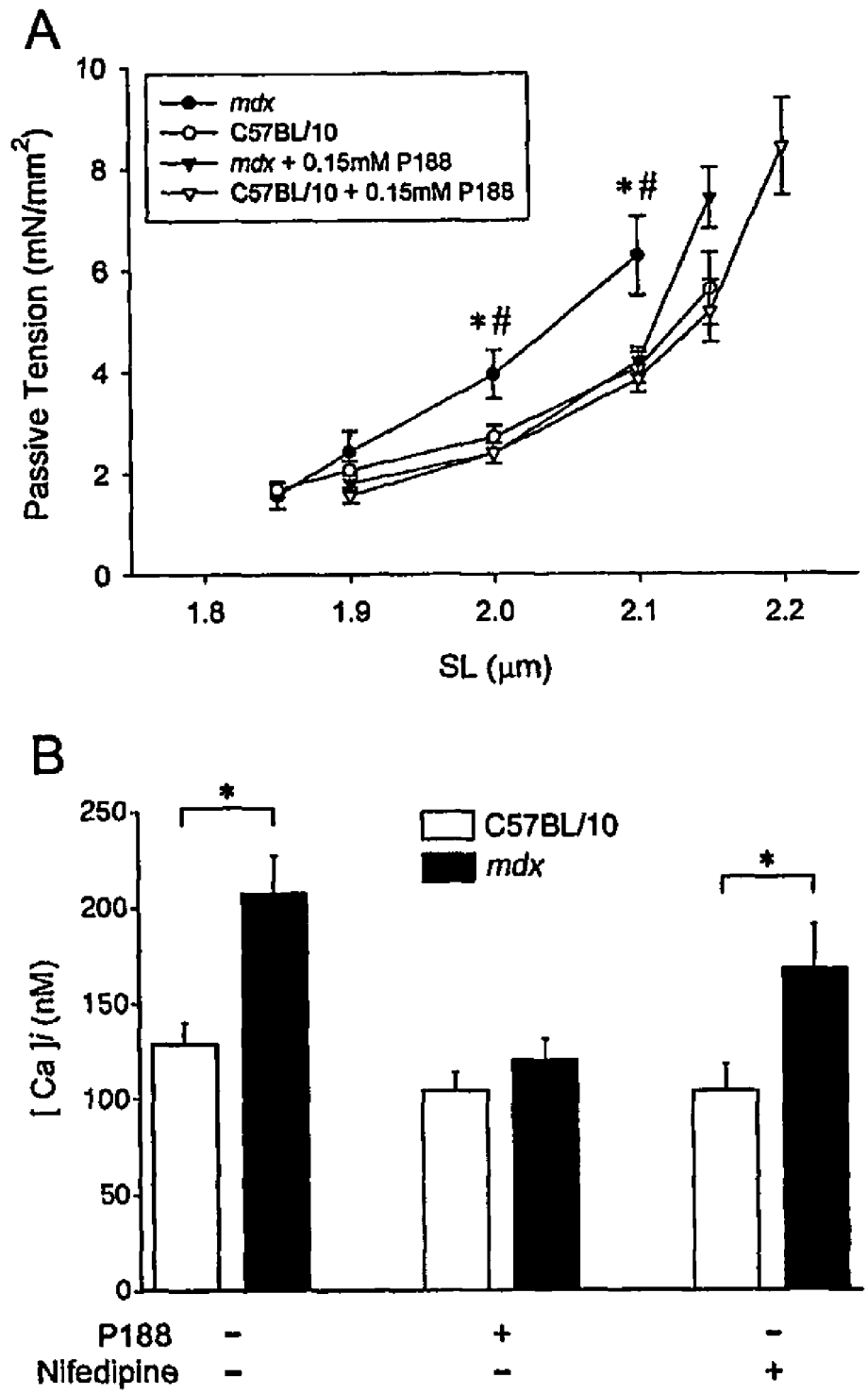
FIG. 2 shows passive tension and $[Ca^{2+}]_i$ during SL stretch in control and mdx single cardiac myocytes. A. Effects of P188 on passive tension-extension relationships. Asterisks indicate mdx greater than control (SLs 2.0 and 2.1 µm), and #'s indicate mdx+P188 less than mdx non-treated, p<0.05. B. Summary of effects of P188 and nifedipine on $[Ca^{2+}]_i$ in myocytes upon SL stretch to 2.1 µm. Asterisks indicate mdx greater than BL/10, p<0.05.

The results showed that peak isometric twitch tension is not different between control and mdx myocytes (3.6±0.7 and 4.4±0.8 mN/mm², respectively) indicating that excitation-contraction coupling and force generation/transmission are normal in mdx myocytes. Dystrophin-deficiency did, however, cause significant effects upon passive physiological stretches in myocyte SL length (See FIG. 1B). With passive excursions from resting SL of 1.8 µm to longer SLs, mdx myocytes developed significantly increased tension compared to control myocytes (See FIG. 2A). This is in contrast to previous studies on skeletal myotubes, where dystrophic muscles were found to be more compliant than control muscles (See, e.g., Pasternak et al., J Cell Biol 128, 355-61 (1995)). Stretches to SL>2.1 µm and beyond resulted in mdx myocytes becoming unstable, with increased $[Ca^{2+}]_i$, fibrillations, eventual calcium overload, and subsequent contracture and mytocyte death (See FIG. 1). Reducing extracellular $Ca^{2+}$ from 1.8 to 0.2 mM shifted the tension-extension curves rightward permitting stretches up to 2.3 µm in both mdx and control myocytes, indicating an important role of extracellular calcium in mediating the reduced compliance of mdx myocytes.

Thus, the present invention demonstrates a primary defect in cell compliance in single isolated mdx myocytes, with increased susceptibility to stretch-mediated membrane instability and calcium-dependent hyper-contracture.

Example 3

Stabilization of mdx Myocyte Membranes

Next, it was determined whether a membrane repair approach (e.g., a chemical-based membrane repair approach) would have efficacy in isolated mdx myocytes. The nonionic triblock co-polymer Poloxamer 188 [P188; poly(ethylene oxide)$_{70}$-poly(propylene oxide)$_{35}$-poly(ethylene oxide)$_{70}$; MW≈8400 g/mol)], which was previously shown to insert into artificial lipid monolayers and repair damaged biological membranes (See, e.g., Wu, G. et al., Phys Rev Lett 93, 028101 (2004); Lee et al., Proc Natl Acad Sci U S A 89, 4524-8 (1992)), was assessed for its ability to stabilize mdx myocyte membranes during physiological loading conditions in vitro (See FIG. 2A). Within the physiologically relevant SL range of 1.8-2.1 µm, 0.15 mM P188 (See, e.g., Lee et al., Ann N Y Acad Sci 888, 266-73 (1999)) fully restored mdx myocyte compliance and $[Ca^{2+}]_i$ to control levels (See FIG. 2A). P188 also significantly improved twitch tension performance after a lengthening contraction. P188 had no effect on C57BL/10 myocyte compliance within this SL range (See FIG. 2A). The increase in $[Ca^{2+}]_i$ resulting from passive stretch is significantly greater in mdx myocytes, and this is corrected by P188.

To further address the mechanism of calcium entry, myocytes were treated with the L-type $Ca^{2+}$ channel blocker nifedipine. In contrast to P188, heightened $[Ca^{2+}]_i$ upon SL stretch was not blocked by nifedipine (See FIG. 2B), suggesting elevated $[Ca^{2+}]_i$ may arise from non-DHP sensitive channels, or more likely from small tears in the membrane that are prevented by P188 in mdx mycoytes.

Example 4

Prevention of Cardiac Dysfunction in mdx Mice

Figure 3:
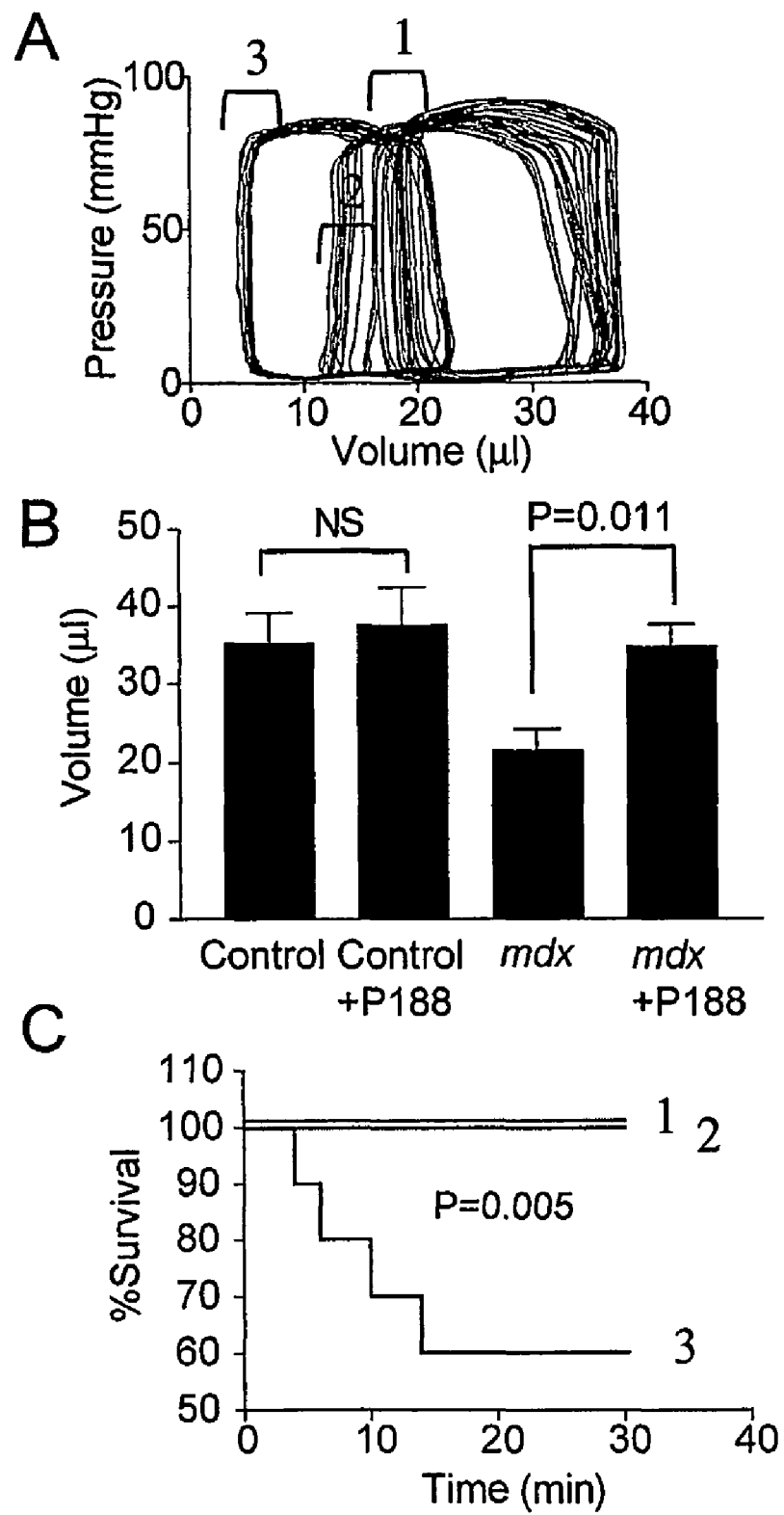
FIG. 3 shows acute effects of P188 on in vivo hemodynamics and mdx survival. A. Representative pressure-volume loops in control (1) and mdx in the presence or absence of acute infusion of P188 (2 and 3, respectively). B. Summary of left ventricular end-diastolic volumes following the infusion of P188 in control and mdx mice. C. Kaplan-Meier survival analysis during 42 µg/kg/min dobutamine infusion. Control (1), mdx (3), mdx+P188 (2). Mice were removed from the study when systolic pressures dropped below 60 mmHg.
Figure 5:
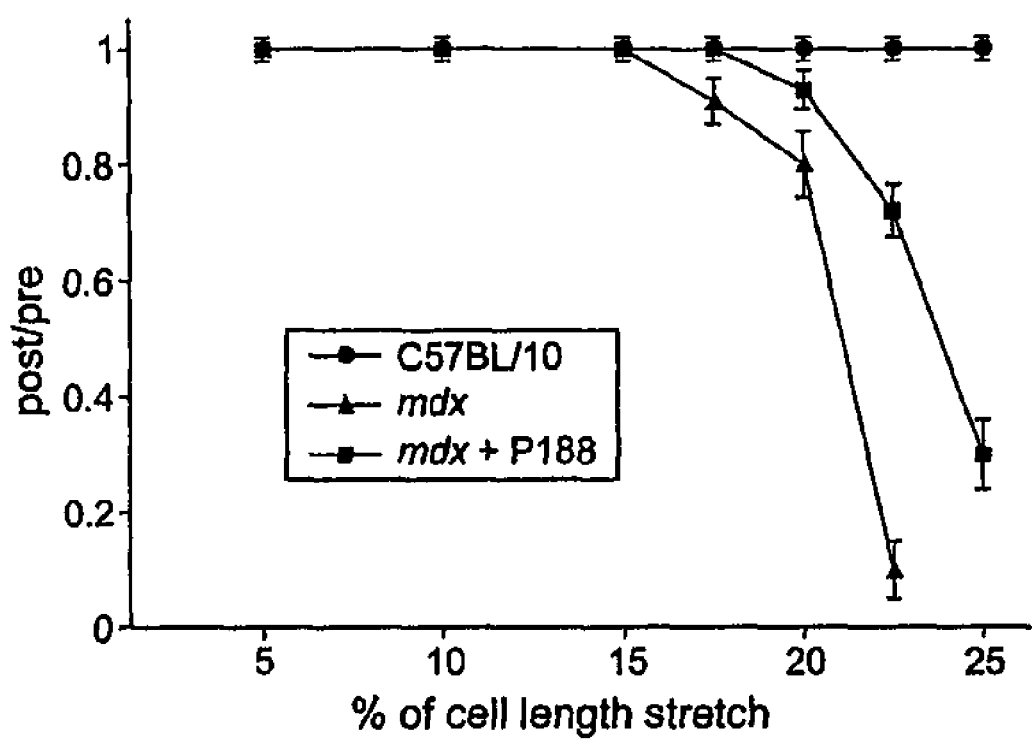
FIG. 5 shows protective effects of P188 on twitch force deficit after single lengthening-contraction in mdx cardiac myocytes. Isometric twitch tension was obtained, followed by single lengthening contraction during a twitch. Post-stretch isometric twitch tension was then recorded. Post-stretch twitch amplitude/pre-stretch twitch amplitude (post/pre) was plotted as a function of the magnitude to the stretch.

It was determined whether these cellular effects of P188 to prevent stretch-induced membrane instability in mdx cardiac myocytes would translate to preventing cardiac dysfunction in mdx mice in vivo. Baseline left ventricular hemodynamic performance was depressed in mdx mice, including reduced left ventricular end-diastolic volume (LVEDV) (See FIG. 3; Table 1). Pre-treatment by intravenous infusion of P188 increased LVEDV to levels seen in control hearts. It was hypothesized that the lower LVEDV in mdx hearts is an organ level manifestation of the membrane defect observed in single isolated myocytes, and that the acute remediation of LVEDV in the mdx heart is a direct effect of P188 to restore normal compliance in single mdx cardiac myocytes (See FIG. 2).

Acute cardiomyopathy and failure can be incited by cardiovascular stressors in mdx mice (See, e.g., Danialou, et al., Faseb J 15, 1655-7 (2001)). Therefore, it was tested whether an acute dobutamine stress challenge in vivo would cause acute cardiac failure, and if this phenotype could be blocked by P188. Untreated mdx mice had very attenuated response to the dobutamine infusion and a significant incidence of acute cardiac failure (See FIG. 3C) during the 30-minute stress-test regime. Pre-treatment of mdx animals by intravenous infusion of P188 immediately improved hemodynamic response to dobutamine infusion, and conferred protection from dobutamine-induced acute heart failure in vivo (p=0.005; See FIG. 3C).

TABLE 1

Summary of baseline hemodynamic data. Date are mean ± SEM.

|  | C57BL/10 (n = 13) | C57BL/10 + Poloxamer 188 (n = 7) | mdx (n = 13) | mdx + Polxamer 188 (n = 11) |
|---|---|---|---|---|
| Heart Rate (bpm) | 598 ± 13 | 600 ± 7 | 582 ± 10 | 585 ± 13 |
| End-Systolic Volume (µl) | 19 ± 2 | 19 ± 4 | 7 ± 1 | 13 ± 3 |
| End-Diastolic Volume (µl) | 36 ± 5 | 36 ± 4 | 22 ± 3 | 34 ± 3 |
| Maximal Pressure (mmHg) | 107 ± 4 | 115 ± 6 | 89 ± 2 | 89 ± 3 |
| Minimal Pressure (mmHg) | 2.1 ± 0.3 | 1.7 ± 0.9 | 2.2 ± 0.4 | 3.5 ± 0.4 |
| Stroke Volume (µl) | 19 ± 2 | 19 ± 3 | 16 ± 2 | 24 ± 2 |
| $(dP/dt)_{Max}$ (mmHg/s) | 11,440 ± 660 | 13,390 ± 460 | 10,110 ± 619 | 10,880 ± 610 |
| $(dP/dt)_{Min}$ (mmHg/s) | −11,420 ± 616 | −11,810 ± 440 | −8,140 ± 580 | −7,110 ± 390 |

Example 5

Figure 6:
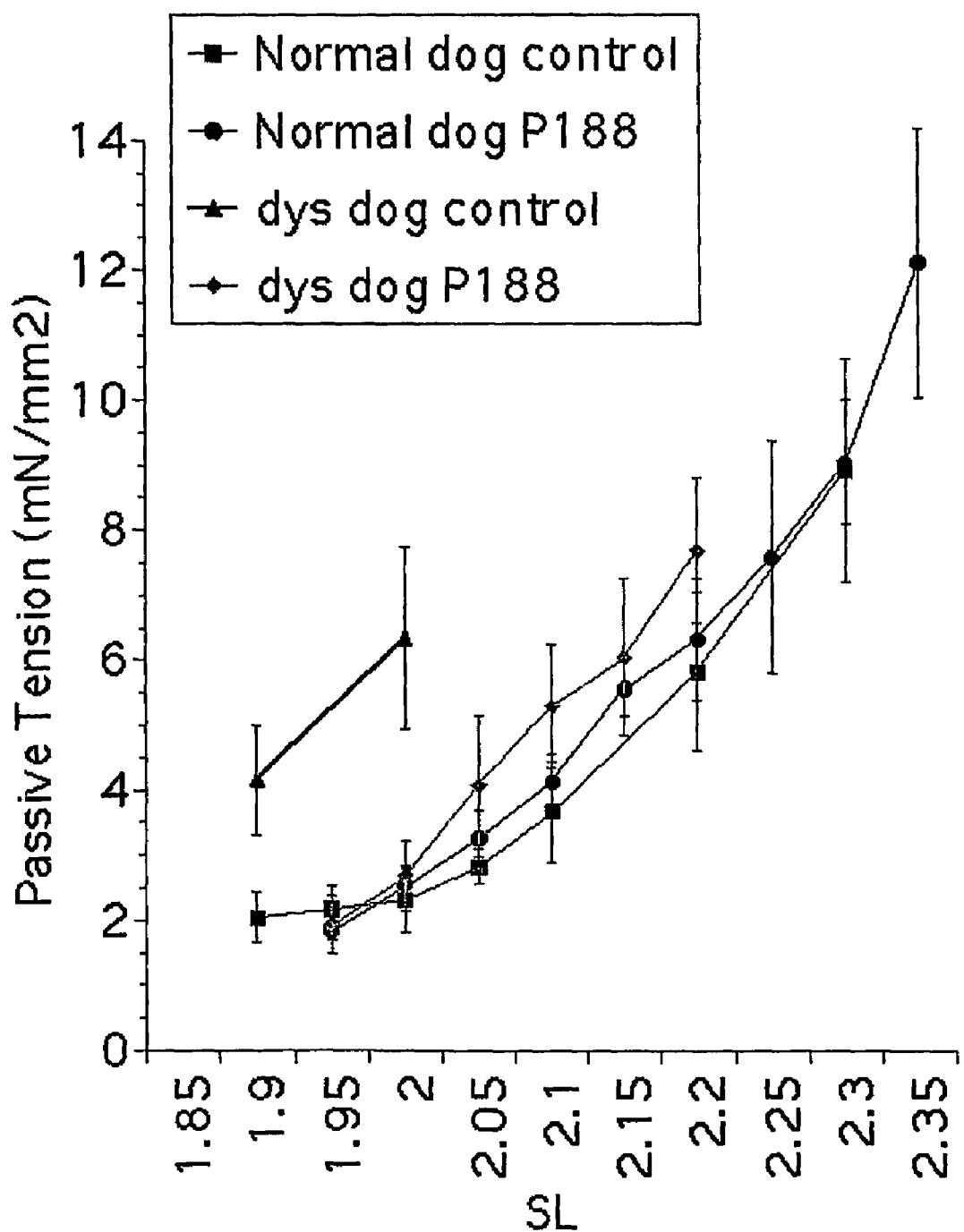
FIG. 6 shows the effects of P188 on passive tension-extension relationships in single membrane intact cardiac myocytes from normal and dystrophic dogs.

Administration of Poloxamer Restores Passive Mechanical Defects in a Canine Model of Cardiomyopathy The effects of P188 on passive tension-extension relationships in single membrane intact cardiac myocytes from normal and dystrophic dogs were studied. Studies in isolated ventricular myocytes from dystrophin-deficient golden retriever dog model (GRMD, See, e.g., Howell et al., Hum Gene Ther. 1998; 9: 629-634) animals show that the passive tension-extension curve is markedly upward and left-ward shifted compared to control dog myocytes (See, FIG. 6). Thus, the present invention provides that the cellular compliance defect noted in cardiac myocytes from the mdx mouse model is much more pronounced in dystrophic myocytes from GRMD dogs.

Next, it was determined whether polaxamer treatment (e.g., administration of a composition comprising a poloxamer) using P188 could improve myocyte function. It was observed that P188 (150 μM) restores cellular compliance and function, as manifested in the shape and position of the passive tension-extension curve back nearly completely to control/normal even in these more severely affected canine myocytes that have pronounced cardiomyopathy. This data demonstrates that the magnitude of the corrective effect resulting from administration of a poloxamer to a dystrophic subject (e.g., P188's effect) is comparatively greater in canine dystrophic myocytes as compared to mouse dystrophic myocytes. Thus, the present invention demonstrates that single cardiac myocytes from GRMD animals are severely affected in terms of passive mechanical properties, and that these passive mechanical defects are corrected and restored by administration of P188.

Example 6

Figure 7:
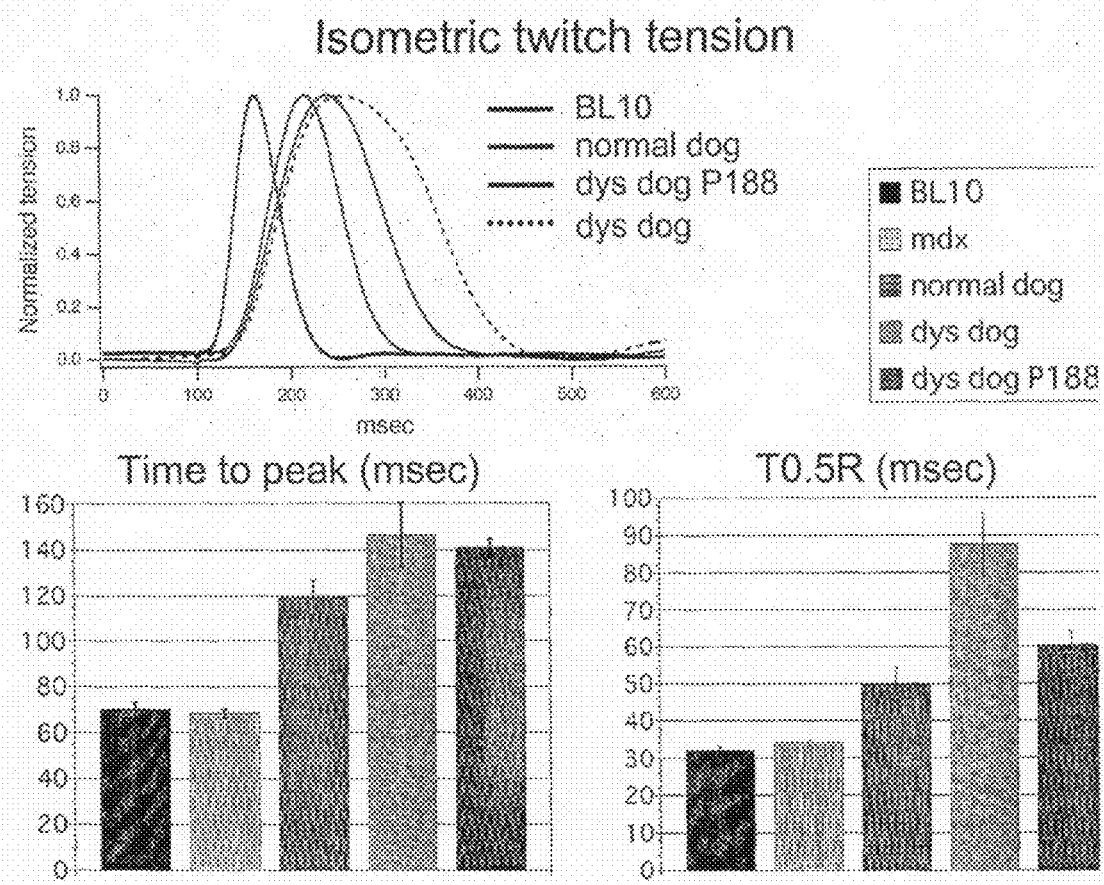
FIG. 7 shows isometric twitch properties of single myocytes from control and dystrophic dogs.

Administration of Poloxamer Corrects Slow Relaxation Performance in Dystrophic Canine Myocytes It was next determined whether P188 would alter the isometric twitch contractile properties of membrane intact single cardiac myocytes from normal and dystrophic dogs. Data generated during the development of the present invention indicates that dystrophin deficiency has a profound effect to slow relaxation performance in single myocytes under physiological load. More importantly, administration of a poloxamer (P188) acutely corrected this relaxation defect (See FIG. 7). Although an understanding of the mechanism is not necessary to practice the present invention and the present invention is not limited to any particular mechanism of action, in some embodiments, administration of a poloxamer (P188) corrects defects of contraction induced membrane instability and consequent $Ca^{2+}$ entry (e.g., calcium overload) thereby preventing alteration of mechanical properties (e.g., diastolic dysfunction) of an intact dystrophic heart (e.g., cardiac myocytes and tissue).

All publications and patents mentioned in the above specification are herein incorporated by reference. Various modifications and variations of the described methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of increasing left ventricular diastolic volume in a dystrophin deficient subject consisting of administering to said subject a composition consisting of poloxamer-188 and a buffer.

2. The method of claim 1, wherein administering said poloxamer reduces intracellular calcium concentration in dystrophin-deficient cardiac myocytes in said subject.

3. The method of claim 2, wherein reducing intracellular calcium concentration in dystrophin-deficient myocytes reduces said subject's susceptibility to calcium overload.

4. The method of claim 1, wherein said composition is administered via intravenous administration.

5. The method of claim 1, wherein said improvement in left ventricular function comprises an improvement in baseline hemodynamic performance in said subject.

6. The method of claim 1, wherein said dystrophin deficient subject is a human subject with Duchene muscular dystrophy.

7. The method of claim 2, wherein said lowering intracellular calcium concentration in dystrophin deficient cardiac myocytes prevents remodelling or reverses remodelling of cardiac muscle tissue in said subject.

8. The method of claim 1, wherein said poloxamer is a purified poloxamer.

9. The method of claim 1, wherein said poloxamer is a fractionated poloxamer.

10. A method of increasing left ventricular diastolic volume in a subject with Duchene muscular dystrophy consisting of administering to said subject a composition consisting of poloxamer-188 and a buffer.

11. The method of claim 10, wherein the poloxamer-188 is a purified or fractionated poloxamer.

12. The method of claim 10, wherein the administration comprises intravenous administration.

* * * * *